United States Patent
Bander

(10) Patent No.: US 6,649,163 B1
(45) Date of Patent: *Nov. 18, 2003

(54) TREATMENT AND DIAGNOSIS OF CANCER

(75) Inventor: Neil H. Bander, Chappaqua, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/357,707

(22) Filed: Jul. 20, 1999

Related U.S. Application Data

(60) Division of application No. 08/895,914, filed on Jul. 17, 1997, now Pat. No. 6,136,311, which is a continuation-in-part of application No. 08/838,682, filed on Apr. 9, 1997, now Pat. No. 6,107,090.
(60) Provisional application No. 60/022,125, filed on Jul. 18, 1996, and provisional application No. 60/016,976, filed on May 6, 1996.

(51) Int. Cl.⁷ ............... A61K 39/395; C07K 16/00; C12P 21/08
(52) U.S. Cl. ............... 424/138.1; 424/130.1; 424/141.1; 424/155.1; 530/387.1; 530/387.7; 530/388.1; 530/388.8
(58) Field of Search ............... 424/130.1, 138.1, 424/141.1, 155.1, 178.1, 181.1; 530/387.1, 387.7, 388.1, 388.8

(56) References Cited

U.S. PATENT DOCUMENTS

| | | |
|---|---|---|
| 4,454,106 A | 6/1984 | Gansow et al. |
| 4,472,509 A | 9/1984 | Gansow et al. |
| 4,814,275 A | 3/1989 | Durda et al. |
| 4,855,353 A | 8/1989 | Kurami et al. |
| 4,863,851 A | 9/1989 | McEwan et al. |
| 4,863,854 A | 9/1989 | Mattes et al. |
| 4,885,363 A | 12/1989 | Tweedle et al. |
| 5,013,645 A | 5/1991 | Kim |
| 5,053,503 A | 10/1991 | Dean et al. |
| 5,057,302 A | 10/1991 | Johnson et al. |
| 5,118,611 A | 6/1992 | Smith et al. |
| 5,130,118 A | 7/1992 | Johnson et al. |
| 5,162,504 A | 11/1992 | Horoszewicz |
| 5,198,208 A | 3/1993 | Berg et al. |
| 5,208,324 A | 5/1993 | Klaveness et al. |
| 5,217,704 A | 6/1993 | Johnson et al. |
| 5,227,471 A | 7/1993 | Wright, Jr. |
| 5,229,289 A | 7/1993 | Kjeldsen et al. |
| 5,314,996 A | 5/1994 | Wright, Jr. |
| 5,342,924 A | 8/1994 | Chang |
| 5,419,893 A | 5/1995 | Berg et al. |
| 5,474,756 A | 12/1995 | Tweedle et al. |

(List continued on next page.)

FOREIGN PATENT DOCUMENTS

| | | |
|---|---|---|
| EP | 0 208 531 | 1/1987 |
| EP | 0 232 751 | 8/1987 |
| EP | 0 233 619 | 8/1987 |
| EP | 0 279 397 | 8/1988 |
| EP | 0 299 795 | 1/1989 |
| EP | 0 315 188 | 5/1989 |
| EP | 0 382 583 | 8/1990 |
| EP | 0 392 423 | 10/1990 |
| EP | 0 466 200 | 1/1992 |
| EP | 0 495 878 | 7/1992 |
| EP | 0 594 739 | 5/1994 |
| EP | 0 292 689 | 11/1998 |
| EP | 0 882 454 | 12/1998 |
| WO | WO 86/06384 | 11/1986 |
| WO | WO 88/02635 | 4/1988 |
| WO | WO 89/00557 | 1/1989 |
| WO | WO 89/06979 | 8/1989 |
| WO | WO 91/15466 | 10/1991 |
| WO | WO 93/17715 | 9/1993 |
| WO | WO 93/19668 | 10/1993 |
| WO | WO 94/04702 | 3/1994 |
| WO | WO 94/09820 | 5/1994 |
| WO | WO 94/26297 | 11/1994 |
| WO | WO 95/26206 | 10/1995 |
| WO | WO 95/31444 | 11/1995 |
| WO | WO 96/26272 | 8/1996 |
| WO | WO 96/39185 | 12/1996 |
| WO | WO 96/40245 | 12/1996 |
| WO | WO 97/32862 | 9/1997 |
| WO | WO 97/35616 | 10/1997 |
| WO | WO 99/43710 | 9/1999 |
| WO | WO 00/50457 | 8/2000 |
| WO | WO 00/52473 | 9/2000 |
| WO | WO 00/74729 | 12/2000 |

OTHER PUBLICATIONS

Chang et al., "Five Different Anti–Prostate–specific Membrane Antigen (PSMA) Antibodies Confirm PSMA Expression in Tumor–associated Neovasculature," *Cancer Res.*, 59:3192–3198 (1999).

Coleman et al., "Fundamental Immunology," Wm. C. Brown Publishers, p. 76.

(List continued on next page.)

*Primary Examiner*—Anthony C. Caputa
*Assistant Examiner*—Gary Nickol
(74) *Attorney, Agent, or Firm*—Fish & Richardson P.C.

(57) ABSTRACT

The present invention is directed to the use of antibodies or binding portions thereof, probes, ligands, or other biological agents which either recognize an extracellular domain of prostate specific membrane antigen or bind to and are internalized with prostate specific membrane antigen. These biological agents can be labeled and used for detection of cancerous tissues, particularly cancerous tissues proximate to or containing vascular endothelial cells, which express an extracellular domain of prostate specific membrane antigen. The labeled biological agents can also be used to detect normal, benign hyperplastic, and cancerous prostate epithelial cells or portions thereof. They also can be used alone or bound to a substance effective to ablate or kill such cells as a therapy for prostate or other cancers. Also disclosed are four hybridoma cell lines, each of which produces a monoclonal antibody recognizing extracellular domains of prostate specific membrane antigens of normal, benign hyperplastic, and cancerous prostate epithelial cells or portions thereof.

109 Claims, 12 Drawing Sheets

U.S. PATENT DOCUMENTS

| | | | |
|---|---|---|---|
| 5,489,525 A | 2/1996 | Pastan | |
| 5,531,978 A | 7/1996 | Berg et al. | |
| 5,538,866 A | 7/1996 | Israeli et al. | |
| 5,565,562 A | 10/1996 | Parker et al. | |
| 5,578,484 A | 11/1996 | Horoszewicz | |
| 5,599,677 A | 2/1997 | Dowell et al. | |
| 5,639,879 A | 6/1997 | Mease et al. | |
| 5,660,827 A | 8/1997 | Thorpe et al. | |
| 5,674,470 A | 10/1997 | Tweedle et al. | |
| 5,697,902 A | 12/1997 | Goldenberg | |
| 5,763,202 A | 6/1998 | Horoszewicz | |
| 5,776,427 A | 7/1998 | Thorpe et al. | |
| 5,804,602 A | 9/1998 | Slusher et al. | |
| 5,846,519 A | 12/1998 | Tweedle et al. | |
| 5,855,866 A | 1/1999 | Thorpe et al. | 424/1.49 |
| 5,863,538 A | 1/1999 | Thorpe et al. | |
| 5,877,289 A | 3/1999 | Thorpe et al. | 530/387.1 |
| 5,935,818 A | 8/1999 | Israeli et al. | |
| 5,958,474 A | 9/1999 | Lee et al. | |
| 5,965,132 A | 10/1999 | Thorpe et al. | |
| 6,004,554 A | 12/1999 | Thorpe et al. | |
| 6,004,555 A | 12/1999 | Thorpe et al. | |
| 6,022,524 A | 2/2000 | Maisano et al. | |
| 6,036,955 A | 3/2000 | Thorpe et al. | |
| 6,051,230 A | 4/2000 | Thorpe et al. | |
| 6,093,399 A | 7/2000 | Thorpe et al. | |
| 6,143,274 A | 11/2000 | Tweedle et al. | |
| 6,150,508 A | 11/2000 | Murphy et al. | |
| 6,261,535 B1 | 7/2001 | Thorpe et al. | |
| 6,331,175 B1 | 12/2001 | Goldenberg | |

OTHER PUBLICATIONS

Harlow et al., "Antibodies: A laboratory manual", Cold Spring Harbor Laboratory, pp. 139–243.

Heston, "Characterization and Glutamyl Preferring Carboxypeptidase Function of Prostate Specific Membrane Antigen: A Novel Folate Hydrolase" (*Urology* 49 (Supp. 3A): 104–112; 106 (1997).

Horoszewicz et al. "Monoclonal Antibodies to a New Antigenic Marker in Epithelial Prostatic Cells and Serum of Prostatic Cancer Patients," *Anticancer Research*, 7:927–936 (1987).

Israeli et al., "Expression of the Prostate–Specific Membrane Antigen", *Cancer Research*, 54:1807–1811 (1994).

Israeli et al., "Molecular Cloning of a Complementry DNA Encoding a Prostate–Specific Membrane Antigen", *Cancer Research*, 53:227–230 (1993).

Jain, R.K. "Vascular and interstitial barriers to delivery of therapeutic agents in tumors" Cancer and Metastasis Reviews, vol. 9, p. 253–266.

Liu, et al., "Constitutive and Antibody–Induced Internalization of Prostate–Specific Membrane Antigen," *Cancer Res.*, 58:4055–60 (1998).

Liu, et. al., "Monoclonal Antibodies to the Extracellular Domain of Prostate–specific Membrane Antigen also React with Tumor Vascular Endothelium," *Cancer Res.* 57:3629–34 (1997).

Murphy et al., "Measurement of Prostate–Specific Membrane Antigen in the Serum With a New Antibody," *The Prostate*, 28:266–271 (1996).

Rochon et al., "Western Blot Assay for Prostate–Specific Membrane Antigen in Serum of Prostate Cancer Patients," *The Prostate*, 25:219–223 (1994).

Schlom, "Monoclonal antibodies: They're more and less than you think", in Molecular Foundations of Oncology, ed. by Broder, William & Wilkins.

Silver et al., "Prostate–specific Membrane Antigen Expression in Normal and Malignant Human Tissues," *Clin. Cancer Res.* 3:81–85 (1997).

Troyer et al., "Biochemical Characterization and Mapping of the 7EII–C5.3 Epitope of the Prostate–Specific Membrane Antigen," *Urol Oncol.*, 1:29–37 (1995).

Troyer et al., "Detection and Characterization of the Prostate–Specific Membrane Antigen (PSMA) in Tissue Extracts and Body Fluids," *Int. J. Cancer*, 62:552–558 (1995).

Troyer et al., "Location of prostate–specific membrane antigen in the LNCaP prostate carcinoma cell line," *Prostate*, 30:232–242. (1997).

Wright et al., "Expression of Prostate–Specific Membrane Antigen in Normal, Benign, and Malignant Prostate Tissues," *Urol Oncol.*, 1:18–28 (1995).

Yang et al., AACR Abstract #2996 (1998); "Alpha particle emitter therapy of micrometastases: $^{213}$Bi–J5 . . . (anti–P-SMA) treatment of LnCaP spheroids," Proceedings of the American Association for Cancer Research, 39:440 (1998).

Dillman R. O. et al., "Human Anti–Mouse Antibody Response in Cancer Patients Following Single Low–Dose Injections of Radiolabeled Murine Monoclonal Antibodies-"Cancer BioTherapy, 9(1):17–28 (1994).

Dillman et al., "Toxicities associated with monoclonal antibody infusions in cancer patients."Molecular Biother, 1:81–85 (1998).

Leung, J. et al., "Selection of a monoclonal antibody to a new prostate cancer marker for in vivo clinical trials"(abstract) $6^{th}$ Int. Congr. Immunol., p. 516 (1986).

Wang et al., "Monoclonal Antibody Assays for Prostatic Tumor", Immunol Ser. 39:195–219 (1998).

Greenspan et al ( Nature Biotechnoogy 7:936 937 (1999).*

Barren et al., (1997), "Monoclonal Antibody 7E11.C5 Staining of Viable LNCaP Cells", Prostate 30(1):65–8.

Carter et al. (1996), "Prostate–specific Membrane Antigen is a Hydrolase with Substrate and Pharmacologic Characteristics of a Neuropeptidase", Proc. Natl. Acad. Sci. U.S.A. 93:749–751.

Diamond et al. (1997), "Monoclonal Antibody 225 Blockade of Prostate Specific Membrane Antigen (PSM) Expression: Potential Novel Theraphy for Prostate Cancer", Journal of Urology 157(4 suppl):226 (Abstract 884).

Fair et al. (1997), "Prostate Specific Membrane Antigen", Prostate 32(2):140–8.

Israeli et al. (1997), "Prostate Specific Membrane Antigen and Other Prostatic Tumor Markers on the Horizon", Urological Clinics of North America 24(2):439–50.

Leek et al. (1995), "Prostate–Specific Membrane Antigen: Evidence for the Existence of a Second Related Human Gene", British Journal of Cancer 72:583–588.

Murphy et al. (1995), "Comparison of Prostate Specific Antigen, Prostate Specific Membrane Antigen, and LNCaP–Based Enzyme–Linked Immunosorbent Assays in Prostatic Cancer Patients and Patients With Benigen Prostatic Enlargement", The Prostate 26:164–168.

Murphy et al. (1995), "Comparison of Prostate Specific Membrane Antigen, and Prostate Specific Antigen Levels in Prostatic Cancer Patients", Anticancer Res. 15:1473–1480.

Pinto et al. (1996), "Prostate–Specific Membrane Antigen: A Novel Folate Hydrolase in Human Prostatic Carcinoma Cells", Clincal Cancer Research 2(9):1445–51.

Su et al. (1995), "Alternatively Spliced Variants of Prostate-specific Membrane Antigen RNA: Ratio of Expression as a Potential Measurement of Progression", Cancer Research 55:1441–1443.

Troyer et al. (1994), "Subcellular Localization of the 7E11–C5 Prostate Specific Antigen", Pro. Am. Assoc. Cancer Research 35:283 (Abstract 1688).

Uria et al. (1997), "Prostate Specific Membrane Antigen in Breast Carinoma", The Lancet 349(9065):1601.

Wright (1990), "Characterization of a New Prostate Carcinoma–Associated Marker: 7E11–C5", Antibody Immunoconjugates and RadioPharmaceuticals 3:Abstract 193.

* cited by examiner

LIPMAN-PEARSON PROTEIN ALIGNMENT
KTUPLE: 2; GAP PENALTY: 4; GAP LENGTH PENALTY: 12

| SEQ1(1>115)<br>J591VH.PRO | SEQ2(1>125)<br>MUVHIIA.PRO | SIMILARITY<br>INDEX | GAP<br>NUMBER | GAP<br>LENGTH | CONSENSUS<br>LENGTH |
|---|---|---|---|---|---|
| (1>115) | (1>125) | 75.6 | 2 | 10 | 125 |

```
         10        20        30        40        50
          ↓         ↓         ↓         ↓         ↓
EVQLQQSGPELVKPGTSVRISCKTSGYTFTEYTI-HWVKQSHGKSLEWIGNINPNNGGTT
EVQLQQSGPELVKPG:SV:ISCK:SGYTFT:Y : :WVKQS.GKSLEWIG:INP.NGGT:
EVQLQQSGPELVKPGASVKISCKASGYTFTDYYMNNWVKQSPGKSLEWIGDINPGNGGTS
          ↑         ↑         ↑         ↑         ↑         ↑
          10        20        30        40        50        60

60        70        80        90       100       110
          ↓         ↓         ↓         ↓         ↓         ↓
YNQKFEDKATLTVDKSSSTAYMELRSLTSEDSAVYYCAAG--------WNFDYWGQGTT
YNQKF.:KATLTVDKSSSTAYM:L.SLTSEDSAVYYCA G        ..FDYWGQGTT
YNQKFKGKATLTVDKSSSTAYMQLSSLTSEDSAVYYCARGYYSSSYMAYYAFDYWGQGTT
          ↑         ↑         ↑         ↑         ↑         ↑
          70        80        90       100       110       120

LTVSS
:TVSS
VTVSS
```

FIG. 8

ENZYMES: ALL 74 ENZYMES (NO FILTER):
SETTINGS: LINEAR, CERTAIN SITES ONLY, STANDARD GENETIC CODE

```
                         Alu                                                                         Hph I
                         |                                                                           |
SEQ.ID.NO.9   TTATATGGAGCTGATGGGAACATTGTAATGACCCAATCTCCCAAATCCATGTCCATGTCAGTAGGAGAGA
                                                                                                      70
SEQ.ID.NO.10  AATATACCTCGACTACCCTTGTAACATTACTGGGTTAGAGGGTTTAGGTACAGGTACAGTCATCCTCTCT
SEQ.ID.NO.11   L  Y  G  A  D  G  N  I  V  M  T  Q  S  P  K  S  M  S  M  S  V  G  E
SEQ.ID.NO.12    Y  M  E  L  M  G  T  L  .  .  P  N  L  P  N  P  C  P  C  Q  .  E  R
SEQ.ID.NO.13  I  I  W  S  .  W  E  H  C  N  D  P  I  S  Q  I  H  V  H  V  S  R  R  E

Hae III
                                  | Bsr I
SEQ.ID.NO.9   GGGTCACCTTGACCTGCAAGGCCAGTGAGAATGTGGTTACTTATGTTTCCTGGTATCAACAGAAACCAGA
                                                                                                     140
SEQ.ID.NO.10  CCCAGTGGAACTGGACGTTCCGGTCACTCTTACACCAATGAATACAAAGGACCATAGTTGTCTTTGGTCT
SEQ.ID.NO.11   R  V  T  L  T  C  K  A  S  E  N  V  V  T  Y  V  S  W  Y  Q  Q  K  P  E
SEQ.ID.NO.12    G  S  P  .  P  A  R  P  V  R  M  W  L  L  M  F  P  G  I  N  R  N  Q
SEQ.ID.NO.13   G  H  L  D  L  Q  G  Q  .  .  E  C  G  Y  L  C  F  L  V  S  T  E  T  R

Ava II  Mbo I
                                                                          Bsr I  |Dpn I
                                                       Hpa II             Sau96 I| Bsa0 I
                 Alw26 I  Fok I                       |       |Rsa I            ||Pvu I
SEQ.ID.NO.9   GCAGTCTCCTAAACTGCTGATATACGGGGCATCCAACCGGTACACTGGGGTCCCCGATCGCTTCACAGGC
                                                                                                     210
SEQ.ID.NO.10  CGTCAGAGGATTTGACGACTATATGCCCCGTAGGTTGGCCATGTGACCCCAGGGGCTAGCGAAGTGTCCG
SEQ.ID.NO.11   Q  S  P  K  L  L  I  Y  G  A  S  N  R  Y  T  G  V  P  D  R  F  T  G
SEQ.ID.NO.12    S  S  L  L  N  C  .  Y  T  G  H  P  T  G  T  L  G  S  P  I  A  S  Q  A
SEQ.ID.NO.13  A  V  S  .  T  A  D  I  R  G  I  Q  P  V  H  W  G  P  R  S  L  H  R

Mbo I                                                              Eco57 I
                |Dpn I                               Bsp6 II          Mbo II
SEQ.ID.NO.9   AGTGGATCTGCAACAGATTTCACTCTGACCATCAGCAGTGTGCAGGCTGAAGACCTTGCAGATTATCACT
                                                                                                     280
SEQ.ID.NO.10  TCACCTAGACGTTGTCTAAAGTGAGACTGGTAGTCGTCACACGTCCGACTTCTGGAACGTCTAATAGTGA
SEQ.ID.NO.11   S  G  S  A  T  D  F  T  L  T  I  S  S  V  Q  A  E  D  L  A  D  Y  H
SEQ.ID.NO.12    V  D  L  Q  Q  I  S  L  .  P  S  A  V  C  R  L  K  T  L  Q  I  I  T
SEQ.ID.NO.13  Q  W  I  C  N  R  F  H  S  D  H  Q  Q  C  A  G  .  R  P  C  R  L  S  L

Ava II
                 Alu I  Rsa I                   Sau96 I  Alu I
SEQ.ID.NO.9   GTGGACAGGGTTACAGCTATCCGTACACGTTCGGAGGGGGGACCAAGCTGGAAATAAAACGGGCTGATGC
                                                                                                     350
SEQ.ID.NO.10  CACCTGTCCCAATGTCGATAGGCATGTGCAAGCCTCCCCCCTGGTTCGACCTTTATTTTGCCCGACTACG
SEQ.ID.NO.11   C  G  Q  G  Y  S  Y  P  Y  T  F  G  G  G  T  K  L  E  I  K  R  A  D  A
SEQ.ID.NO.12    V  D  R  V  T  A  I  R  T  R  S  E  G  G  P  S  W  K  .  N  G  L  M
SEQ.ID.NO.13  W  T  G  L  Q  L  S  V  H  V  R  R  G  D  Q  A  G  N  K  T  G  .  C

SEQ.ID.NO.9   TGCACCAACTGTA
                           → 363
SEQ.ID.NO.10  ACGTGGTTGACAT
SEQ.ID.NO.11   A  P  T  V
SEQ.ID.NO.12    L  H  Q  L  Y
SEQ.ID.NO.13  C  T  N  C
```

*FIG. 10*

LIPMAN-PEARSON PROTEIN ALIGNMENT
KTUPLE: 2; GAP PENALTY: 4; GAP LENGTH PENALTY: 12

| SEQ1(1>107)<br>J591VK.PRO | SEQ2(1>111)<br>MUVKV.PRO | SIMILARITY<br>INDEX | GAP<br>NUMBER | GAP<br>LENGTH | CONSENSUS<br>LENGTH |
|---|---|---|---|---|---|
| (1>107) | (1>109) | 60.4 | 2 | 2 | 109 |

```
         10        20        30        40        50
         ↓         ↓         ↓         ↓         ↓
NIVMTQSPKSMSMSVGERVTLTCKAS-ENVVTYVSWYQQKPEQSPKLLIYGASNRYTGVP
:I MTQSP.S:S S:G:RVT:TC:AS :::  .Y::WYQQKP. SPKLLIY AS.  .:GVP
DIQMTQSPSSLSASLGDRVTITCRASQDDISNYLNWYQQKPGGSPKLLIYYASRLHSGVP
         ↑         ↑         ↑         ↑         ↑         ↑
         10        20        30        40        50        60

60        70        80        90        100
         ↓         ↓         ↓         ↓         ↓
DRFTGSGSATDFTLTISSVQAEDLADYHCGQGYSY-PYTFGGGTKLEIK
.RF:GSGS:TD::LTIS::::.ED:A.Y C QG :  P TFGGGTKLEIK
SRFSGSGSGTDYSLTISNLEQEDIATYFCQQGNTLPPRTFGGGTKLEIK
         ↑         ↑         ↑         ↑
         70        80        90        100
```

*FIG. 11*

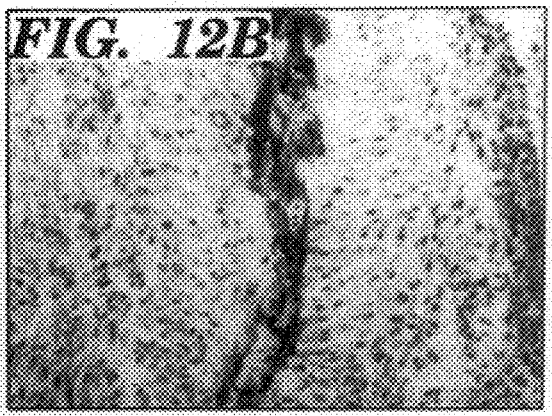
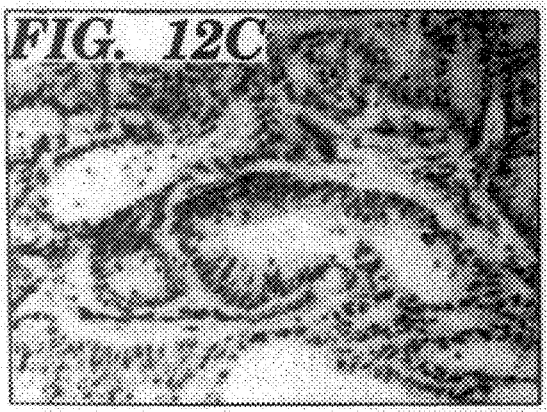
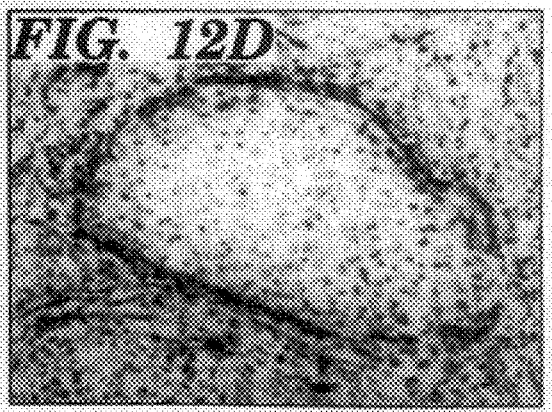
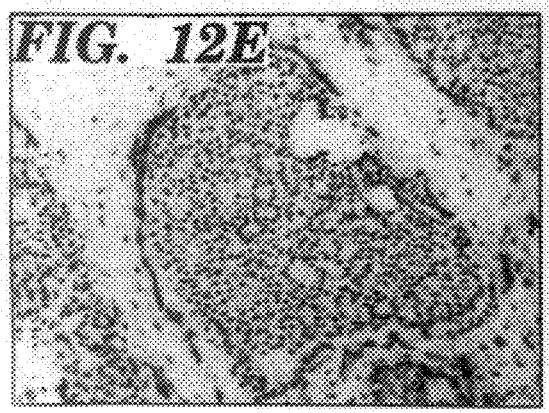

TREATMENT AND DIAGNOSIS OF CANCER

This application is a divisional of application Ser. No. 08/895,914, filed on Jul. 17, 1997, now U.S. Pat No. 6,136,311, which claims the benefit of U.S. Provisional patent application 60/022,125, filed Jul. 18, 1996, and is a continuation-in-part of U.S. patent application Ser. No. 08/838,682, filed Apr. 9, 1997, now U.S. Pat. No. 6,107,090, which claims the benefit of U.S. Provisional patent application Ser. No. 60/016,976, filed May 6, 1996 and U.S. Provisional patent application Ser. No. 60/022, 125, filed Jul. 18, 1996.

FIELD OF THE INVENTION

The present invention relates to the treatment and diagnosis of cancer with biological agents.

BACKGROUND OF THE INVENTION

In spite of improved treatments for certain forms of cancer, it is still a leading cause of death in the United States. Since the chance for complete remission of cancer is, in most cases, greatly enhanced by early diagnosis, it is very desirable that physicians be able to detect cancers before a substantial tumor develops. However, the development of methods that permit rapid and accurate detection of many forms of cancers continues to challenge the medial community. One such illustrative form of cancer is prostate cancer.

Prostate cancer is the most common cancer in men with an estimated 317,000 cases in 1996 in the United States. It is the second leading cause of death among men who die from neoplasia with an estimated 40,000 deaths per year. Prompt detection and treatment is needed to limit mortality caused by prostate cancer.

Detection of Prostate Cancer

When it metastasizes, prostatic cancer has a distinct predilection for bone and lymph nodes. Saitoh et al., "Metastatic Patterns of Prostatic Cancer. Correlation Between Sites And Number Of Organs Involved," Cancer, 54:3078–3084 (1984). At the time of clinical diagnosis, as many as 25% of patients have bone metastasis demonstrable by radionuclide scans. Murphy, G. P., et al., "The National Survey Of Prostate Cancer In The United States By The American College Of Surgeons," J. Urol., 127:928–939 (1982). Accurate clinical evaluation of nodal involvement has proven to be difficult. Imaging techniques such as computed tomography ("CT") or magnetic resonance ("MR") imaging are unable to distinguish metastatic prostate cancer involvement of lymph nodes by criterion other than size (i.e., >1 cm). Therefore, by definition, these imaging modalities are inherently insensitive in the detection of small volume (<1 cm) disease as well as non-specific in the detection of larger volume adenopathy. A recent study assessed the accuracy of MR in patients with clinically localized prostate cancer. Rifkin et al., "Comparison Of Magnetic Resonance Imaging And Ultrasonography In Staging Early Prostate Cancer," N. Engel. J. Med., 323:621–626 (1990). In this study, 194 patients underwent an MR and 185 of these patients had a lymph node dissection. 23 (13%) patients had pathologically involved lymph nodes. MR was suspicious in only 1 of these 23 cases resulting in a sensitivity of 4%. Similar results have also been noted with CT scans. Gasser et al., "MRI And Ultrasonography In Staging Prostate Cancer," N. Engl. J. Med. (Correspondence), 324 (7):49–495 (1991).

The elevation of serum acid phosphatase activity in patients having metastasized prostate carcinoma was first reported by Gutman et al., J. Clin. Invest 17:473 (1938). In cancer of the prostate, prostatic acid phosphatase is released from the cancer tissue into the blood stream with the result that the total serum acid phosphatase level can be greatly increased above normal values. Numerous studies of this enzyme and its relation to prostatic cancer have been made since that time, e.g. Yam, Amer. J. Med. 56:604 (1974). However, the measurement of serum acid phosphatase is elevated in about 65–90 percent of patients having carcinoma of the prostate with bone metastasis; in about 30 percent of patients without roentgenological evidence of bone metastasis; and in about only 5–10 percent of patients lacking clinically demonstrable metastasis.

Prior art attempts to develop a specific test for prostatic acid phosphatase have met with only limited success, because techniques which rely on enzyme activity on a so-called "specific" substrate cannot take into account other biochemical and immunochemical differences among the many acid phosphatases which are unrelated to enzyme activity of prostate origin. In the case of isoenzymes, i.e. genetically defined enzymes having the same characteristic enzyme activity and a similar molecular structure but differing in amino acid sequences and/or content and, therefore, immunochemically distinguishable, it would appear inherently impossible to distinguish different isoenzyme forms merely by the choice of a particular substrate. It is, therefore, not surprising that none of these prior art methods is highly specific for the direct determination of prostatic acid phosphatase activity; e.g. see Cancer 5:236 (1952); J. Lab. Clin. Med. 82:486 (1973); Clin. Chem. Acta. 44:21 (1973); and J. Physiol. Chem. 356:1775 (1975).

In addition to the aforementioned problems of non-specificity which appear to be inherent in many of the prior art reagents employed for the detection of prostate acid phosphatase, there have been reports of elevated serum acid phosphatase associated with other diseases, which further complicates the problem of obtaining an accurate clinical diagnosis of prostatic cancer. For example, Tuchman et al., Am. J. Med. 27:959 (1959) noted that serum acid phosphatase levels appear to be elevated in patients with Gaucher's disease.

Due to the inherent difficulties in developing a "specific" substrate for prostate acid phosphatase, several researchers have developed immunochemical methods for the detection of prostate acid phosphatase. However, the previously reported immunochemical methods have drawbacks of their own which have precluded their widespread acceptance. For example, Shulman et al., Immunology 93:474 (1964) described an immuno-diffusion test for the detection of human prostate acid phosphatase. Using antisera prepared from a prostatic fluid antigen obtained by rectal massage from patients with prostatic disease, no cross-reactivity precipitin line was observed in the double diffusion technique against extracts of normal kidney, testicle, liver, and lung. However, this method has the disadvantages of limited sensitivity, even with the large amounts of antigen employed, and of employing antisera which may cross-react with other, antigenically unrelated serum protein components present in prostatic fluid.

WO 79/00475 to Chu et. al. describes a method for the detection of prostatic acid phosphatase isoenzyme patterns associated with prostatic cancer which obviates many of the above drawbacks. However, practical problems are posed by the need for a source of cancerous prostate tissue from which the diagnostically relevant prostatic acid phosphatase isoenzyme patterns associated with prostatic cancer are extracted for the preparation of antibodies thereto.

In recent years, considerable effort has been spent to identify enzyme or antigen markers for various types of malignancies with the view towards developing specific diagnostic reagents. The ideal tumor marker would exhibit, among other characteristics, tissue or cell-type specificity. Previous investigators have demonstrated the occurrence of human prostate tissue-specific antigens.

Treatment of Prostate Cancer

As described in W. J. Catalona, "Management of Cancer of the Prostate," New Engl. J. Med., 331 (15) :996–1004 (1994), the management of prostate cancer can be achieved by watchful waiting, curative treatment, and palliation.

For men with a life expectancy of less than 10 years, watchful waiting is appropriate where low-grade, low-stage prostate cancer is discovered at the time of a partial prostatectomy for benign hyperplasia. Such cancers rarely progress during the first five years after detection. On the other hand, for younger men, curative treatment is often more appropriate.

Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. However, the use of prostate-specific antigen testing has permitted early detection of prostate cancer. As a result, surgery is less extensive with fewer complications. Patients with bulky, high-grade tumors are less likely to be successfully treated by radical prostatectomy.

After surgery, if there are detectable serum prostate-specific antigen concentrations, persistent cancer is indicated. In many cases, prostate-specific antigen concentrations can be reduced by radiation treatment. However, this concentration often increases again within two years.

Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy.

For treatment of patients with locally advanced disease, hormonal therapy before or following radical prostatectomy or radiation therapy has been utilized. Hormonal therapy is the main form of treating men with disseminated prostate cancer. Orchiectomy reduces serum testosterone concentrations, while estrogen treatment is similarly beneficial. Diethylstilbestrol from estrogen is another useful hormonal therapy which has a disadvantage of causing cardiovascular toxicity. When gonadotropin-releasing hormone agonists are administered testosterone concentrations are ultimately reduced. Flutamide and other nonsteroidal, anti-androgen agents block binding of testosterone to its intracellular receptors. As a result, it blocks the effect of testosterone, increasing serum testosterone concentrations and allows patients to remain potent—a significant problem after radical prostatectomy and radiation treatments.

Cytotoxic chemotherapy is largely ineffective in treating prostate cancer. Its toxicity makes such therapy unsuitable for elderly patients. In addition, prostate cancer is relatively resistant to cytotoxic agents.

Use of Monoclonal Antibodies in Prostate Cancer Detection and Treatment

Theoretically, radiolabeled monoclonal antibodies ("mAbs") offer the potential to enhance both the sensitivity and specificity of detecting prostatic cancer within lymph nodes and elsewhere. While many mAbs have previously been prepared against prostate related antigens, none of these mabs were specifically generated with an imaging objective in mind. Nevertheless, the clinical need has led to evaluation of some of these mAbs as possible imaging agents. Vihko et al., "Radioimaging of Prostatic Carcinoma With Prostatic Acid Phosphatase—Specific Antibodies," Biotechnolocy in Diagnostics, 131–134 (1985); Babaian et al., "Radioimmunological Imaging of Metastatic Prostatic Cancer With 111-Indium-Labeled Monoclonal Antibody PAY 276," J. Urol., 137:439–443 (1987); Leroy et al., "Radioimmunodetection Of Lymph Node Invasion In Prostatic Cancer. The Use Of Iodine 123 (123-I)-Labeled Monoclonal Anti-Prostatic Acid Phosphatase (PAP) 227 A F (ab') 2 Antibody Fragments In Vivo," Cancer, 64:1–5 (1989); Meyers et al., "Development Of Monoclonal Antibody Imaging Of Metastatic Prostatic Carcinoma," The Prostate, 14:209–220 (1989).

In some cases, the monoclonal antibodies developed for detection and/or treatment of prostate cancer recognize antigens specific to malignant prostatic tissues. Such antibodies are thus used to distinguish malignant prostatic tissue (for treatment or detection) from benign prostatic tissue. See U.S. Pat. No. 4,970,299 to Bazinet et al. and U.S. Pat. No. 4,902,615 to Freeman et al.

Other monoclonal antibodies react with surface antigens on all prostate epithelial cells whether cancerous or benign. See U.S. Pat. Nos. 4,446,122 and Re 33,405 to Chu et al., U.S. Pat. No. 4,863,851 to McEwan et al., and U.S. Pat. No. 5,055,404 to Ueda et al. However, the antigens detected by these monoclonal antibodies are present in the blood and, therefore, compete with antigens at tumor sites for the monoclonal antibodies. This causes background noise which makes the use of such antibodies inadequate for in vivo imaging. In therapy, such antibodies, if bound to a cytotoxic agent, could be harmful to other organs.

Horoszewicz et al., "Monoclonal Antibodies to a New Antigenic Marker in Epithelial Prostatic Cells and Serum of Prostatic Cancer Patients," Anticancer Research, 7:927–936 (1987) ("Horoszewicz") and U.S. Pat. No. 5,162,504 to Horoszewicz describe an antibody, designated 7E11, which recognizes prostate specific membrane antigen ("PSMA"). Israeli et al., "Molecular Cloning of a Complementary DNA Encoding a Prostate-specific Membrane Antigen," Cancer Research, 53:227–230 (1993) ("Israeli") describes the cloning and sequencing of PSMA and reports that PSMA is prostate-specific and shows increased expression levels in metastatic sites and in hormone-refractory states. Other studies have indicated that PSMA is more strongly expressed in prostate cancer cells relative to cells from the normal prostate or from a prostate with benign hyperplasia. Furthermore, PSMA is not found in serum (Troyer et al., "Detection and Characterization of the Prostate-Specific Membrane Antigen (PSMA) in Tissue Extracts and Body Fluids," Int. J. Cancer, 62:552–558 (1995)).

These characteristics make PSMA an attractive target for antibody mediated targeting for imaging and therapy of prostate cancer. Imaging studies using indium-labeled 7E11 have indicated that the antibody localizes quite well to both the prostate and to sites of metastasis. In addition, 7E11 appears to have clearly improved sensitivity for detecting lesions compared to other currently available imaging techniques, such as CT and MR imaging or bone scan. Bander, "Current Status of Monoclonal Antibodies for Imaging and Therapy of Prostate Cancer," *Sem. In Oncology*, 21:607–612 (1994).

However, the use of 7E11 and other known antibodies to PSMA to mediate imaging and therapy has several disadvantages. First, PSMA is an integral membrane protein known to have a short intracellular tail and a long extracellular domain. Biochemical characterization and mapping (Troyer et al., "Biochemical Characterization and Mapping of the 7E11-C5.3 Epitope of the Prostate-specific Membrane Antigen," *Urol. Oncol.*, 1:29–37 (1995)) have shown that the epitope or antigenic site to which the 7E11 antibody binds is present on the intracellular portion of the molecule. Because antibody molecules do not, under normal circumstances, cross the cell membrane unless they bind to the extracellular portion of a molecule and become translocated intracellularly, the 7E11 antibody does not have access to its antigenic target site in an otherwise healthy, viable cell.

Consequently, imaging using 7E11 is limited to the detection of dead cells within tumor deposits. Additionally, the therapeutic use of the 7E11 antibody is limited, because only cells that are already dead or tissue containing a large proportion of dead cells can be effectively targeted.

Although the inadequacies and problems in the diagnosis and treatment of one particular type of cancer are the focus of the preceding discussion, prostate cancer is merely a representative model. The diagnosis and treatment of numerous other cancers have similar problems.

The present invention is directed to overcoming the deficiencies of prior art antibodies in diagnosing and treating prostate and other types of cancer.

SUMMARY OF THE INVENTION

One aspect of the present invention relates to a method of ablating or killing cancerous cells. The process involves providing a biological agent which, when contacted with an extracellular domain of prostate specific membrane antigen, recognizes the extracellular domain of prostate specific membrane antigen. These biological agents are contacted with vascular endothelial cells proximate to the cancerous cells under conditions effective to permit both binding of the biological agent to the vascular endothelial cells proximate to the cancerous cells and killing or ablating of the cancerous cells. The biological agent can be used alone or can be bound to a substance effective to kill or ablate the cancerous cells upon binding of the biological agent to vascular endothelial cells that are proximate to the cancerous cells.

In a particularly preferred embodiment of the method of ablating or killing cancerous cells in accordance with the present invention, the biological agent, when contacted with an extracellular domain of prostate specific membrane antigen, binds to and is internalized with the prostate specific membrane antigen of such cells. Preferred biological agents for use in the method of ablating or killing cancerous cells in accordance with the present invention are antibodies or binding portions thereof, probes, or ligands. The methods of the present invention are particularly useful in killing or ablating renal, urothelial, colon, rectal, lung, and breast cancerous cells and cancerous cells of metastatic adenocarcinoma to the liver.

Another aspect of the present invention relates to a method of detecting cancerous tissue in a biological sample. This method involves providing a biological agent which, when contacted with an extracellular domain of prostate specific membrane antigen, binds to the extracellular domain of prostate specific membrane antigen. The biological agent is bound to a label effective to permit detection of vascular endothelial cells proximate to or within the cancerous tissue upon binding of the biological agent to the vascular endothelial cells proximate to or within the cancerous tissue. The biological sample is contacted with the biological agent having a label under conditions effective to permit binding of the biological agent to the vascular endothelial cells proximate to or within the cancerous tissue in the biological sample. The presence of cancerous tissue in the biological sample is detected by detection of the label.

In a particularly preferred embodiment of the method of detecting cancerous tissue in accordance with the present invention, the biological agent is one that, when contacted with an extracellular domain of prostate specific membrane antigen, binds to and is internalized with the prostate specific membrane antigen. Preferred biological agents for use in the method of detecting cancerous tissue in accordance with the present invention are antibodies or binding portions thereof, probes, or ligands. The method is especially useful in detecting renal, urothelial, colon, rectal, lung, and breast cancerous tissue and cancerous tissue of metastatic adenocarcinoma to the liver.

Still another aspect of the present invention relates to a method of ablating or killing normal, benign hyperplastic, and cancerous prostate epithelial cells. The process involves providing a biological agent which recognizes an extracellular domain of prostate specific membrane antigen. The biological agent can be used alone or can be bound to a substance effective to kill the cells upon binding of the biological agent to the cells. These biological agents are then contacted with the cells under conditions effective to permit both binding of the biological agent to the extracellular domain of the prostate specific membrane antigen and killing or ablating of the cells.

In a particularly preferred embodiment of the method of ablating or killing normal, benign hyperplastic, and cancerous prostate epithelial cells in accordance with the present invention, the biological agent binds to and is internalized with the prostate specific membrane antigen of such cells. Preferred biological agents for use in the method of ablating or killing normal, benign hyperplastic, and cancerous prostate epithelial cells in accordance with the present invention are antibodies or binding portions thereof, probes, or ligands.

Another aspect of the present invention relates to a method of detecting normal, benign hyperplastic, and cancerous prostate epithelial cells or portions thereof in a biological sample. This method involves providing a biological agent which binds to an extracellular domain of prostate specific membrane antigen. The biological agent is bound to a label effective to permit detection of the cells or portions thereof upon binding of the biological agent to the cells or portions thereof. The biological sample is contacted with the biological agent having a label under conditions effective to permit binding of the biological agent to the extracellular domain of the prostate specific membrane antigen of any of the cells or portions thereof in the biological sample. The presence of any cells or portions thereof in the biological sample is detected by detection of the label.

In a particularly preferred embodiment of the method of detecting normal, benign hyperplastic, and cancerous prostate epithelial cells in accordance with the present invention, the biological agent binds to and is internalized with the prostate specific membrane antigen of such cells. Preferred biological agents for use in the method of detecting normal, benign hyperplastic, and cancerous prostate epithelial cells in accordance with the present invention are antibodies or binding portions thereof, probes, or ligands.

Another aspect of the present invention pertains to a biological agent that recognizes an extracellular domain of prostate specific membriane antigen. In a preferred embodiment, the isolated biological agent binds to and is internalized with the prostate specific membrane antigen. Preferred isolated biological agents which recognize an extracellular domain of prostate specific membrane antigen in accordance with the present invention are isolated antibodies or binding portions thereof, probes, or ligands. Hybridoma cell lines that produce monoclonal antibodies of these types are also disclosed.

The biological agents of the present invention recognize the extracellular domain of antigens of normal, benign hyperplastic, and cancerous prostate epithelial cells. Unlike the 7E11 antibody, which recognizes an epitope of prostate-associated antigens which are exposed extracellularly only after cell lysis, the biological agents of the present invention bind to antigenic epitopes which are extracellularly exposed in living prostate cells. Using the biological agents of the present invention, living, unfixed normal, benign hyperplastic, and cancerous prostate epithelial cells can be targeted, which makes treatment and diagnosis more effective. In a preferred embodiment for treating prostate cancer, the biological agents of the present invention also bind to and are internalized with the prostate specific membrane antigen, which permits the therapeutic use of intracellularly acting cytotoxic agents.

BRIEF DESCRIPTION OF THE DRAWINGS

FIG. 8 is a comparison of the heavy chain of monoclonal antibody J591 with the consensus sequence for Mouse Heavy Chains Subgroup IIA (designated SEQ. ID. No. 20).

FIG. 10 shows the nucleotide sequences of the kappa light chain of monoclonal antibody J591 (designated SEQ.ID. No. 9), the nucleotide sequence of the corresponding reverse, non-coding strand (designated SEQ. ID. No. 10), and the corresponding deduced amino acid sequence (designated SEQ. ID. Nos. 11, 12, and 13).

FIG. 11 is a comparison of the kappa light chain of monoclonal antibody J591 with the consensus sequence for Mouse Kappa Chains Subgroup V (designated SEQ. ID. No. 21).

FIGS. 12A–12F are micrographs (250×magnification) showing the immunohistochemical reactivity of mAb J591 to neovasculature of various carcinomas.

DETAILED DESCRIPTION OF THE INVENTION

Figure 1:
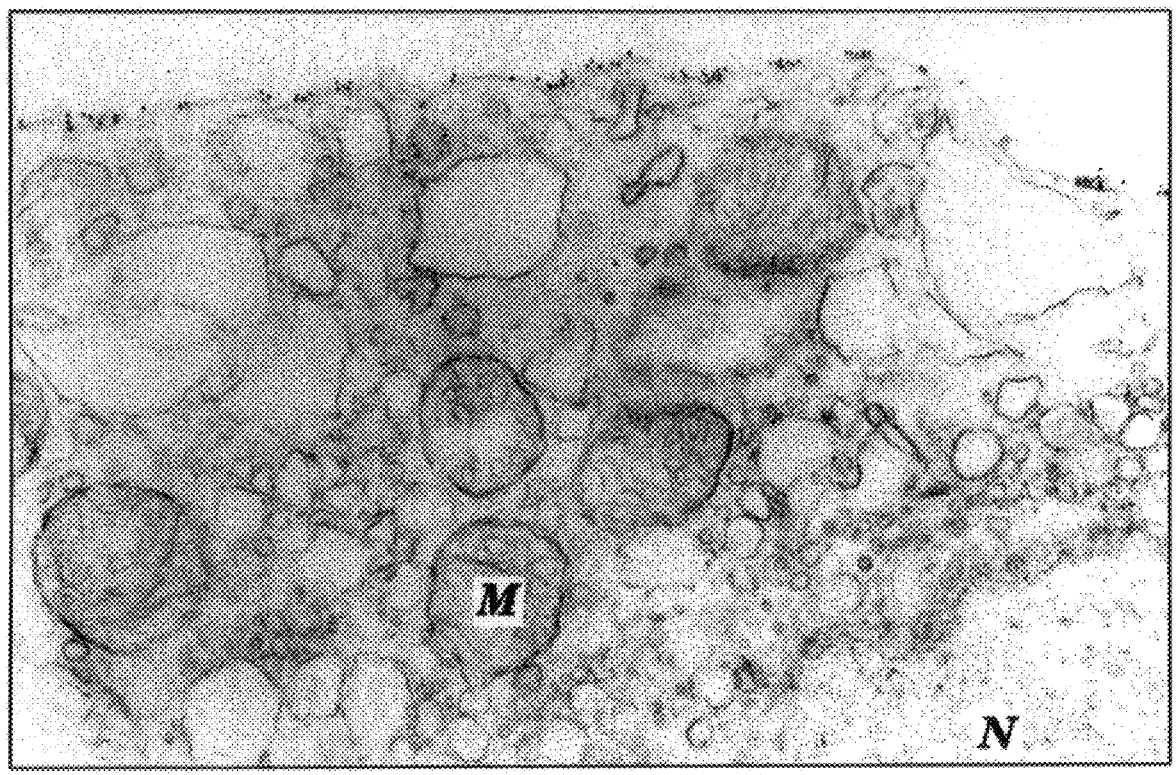
FIG. 1 is an immuno-electron micrograph of gold-labeled monoclonal antibody J591 on the surface of LNCaP. cells after incubation at 4° C.

One aspect of the present invention relates to a method of ablating or killing normal, benign hyperplastic, and cancerous prostate epithelial cells. The process involves providing a biological agent, such as an antibody or binding portion thereof, probe, or ligand, which binds to an extracellular domain of prostate specific membrane antigen of (i.e., a portion of prostate specific membrane antigen which is external to) such cells. The biological agent can be used alone or can be bound to a substance effective to kill the cells upon binding of the biological agent to the cells. These biological agents are then contacted with the cells under conditions effective to permit both binding of the biological agent to the extracellular domain of the prostate specific membrane antigen and killing or ablating of the cells. In its preferred form, such contacting is carried out in a living mammal by administering the biological agent to the mammal under conditions effective to permit both binding of the biological agent to the extracellular domain of the prostate specific membrane antigen and killing or ablating of the cells. Such administration can be carried out orally or parenterally.

In a particularly preferred embodiment of the method of ablating or killing normal, benign hyperplastic, and cancerous prostate epithelial cells in accordance with the present invention, the biological agent binds to and is internalized with the prostate specific membrane antigen of such cells. Again, the biological agent can be used alone. Alternatively, the biological agent can be bound to a substance effective to kill the cells upon binding of the biological agent to prostate specific membrane antigen and upon internalization of the biological agent with the prostate specific membrane antigen.

The mechanism by which the biological agent is internalized with the prostate specific membrane antigen is not critical to the practice of the present invention. For example, the biological agent can induce internalization of the prostate specific membrane antigen. Alternatively, internalization of the biological agent can be the result of routine internalization of prostate specific membrane antigen.

The above-described biological agents (i.e., biological agents, such as an antibody or binding portion thereof, probe, or ligand which, when contacted with an extracellular domain of prostate specific membrane antigen, recognizes the extracellular domain of prostate specific membrane antigen and, preferably, is internalized therewith) can be used to ablate or kill cancerous cells. In this aspect of the present invention, the biological agent can be used alone or can be bound to a substance effective to kill the cancerous cells upon binding of the biological agent to vascular endothelial cells proximate thereto. These biological agents are contacted with vascular endothelial cells proximate to the cancerous cells. The contacting is carried out under conditions that are effective to permit binding of the biological agent to the vascular endothelial cells proximate to the cancerous cells and, in addition, that are effective to kill or ablate the cancerous cells. The mechanism by which the cancerous cells are killed or ablated is not critical to the practice of the present invention. For example, the cancerous cells can be killed or ablated directly by the biological agent as a consequence of their proximity to the vascular endothelial cells to which the biological agent binds. Alternatively, the biological agent can kill, ablate, or otherwise change the properties of the vascular endothelial cells to which it binds so that blood flow to the cancerous cells proximate thereto is stopped or otherwise reduced, thereby causing the cancerous cells to be killed or ablated. Thus, the method of the present invention is particularly useful for killing or ablating vascular endothelial cells in cancerous tissue as well as the cancerous cells contained in cancerous tissue.

In a particularly preferred embodiment of the method of ablating or killing cancerous cells in accordance with the present invention, the biological agent employed is one that, when contacted with an extracellular domain of prostate specific membrane antigen, binds to and is internalized with the extracellular domain of prostate specific membrane antigen. The methods of the present invention are particularly useful to kill or ablate cancerous prostate epithelial cells as well as cancerous cells other than cancerous prostate epithelial cells. Examples of cancerous cells which are not cancerous prostate epithelial cells are renal, urothelial, colon, rectal, lung, and breast cancerous cells and cancerous cells of metastatic adenocarcinoma to the liver. Although the method of the present invention can be used to kill or ablate any cell which expresses an extracellular domain of prostate specific membrane antigen or a portion thereof or whose subsistence is dependent upon cells which express an extracellular domain of prostate specific membrane antigen or a portion thereof, the method of the present invention is particularly useful to kill or ablate cancerous cells, because the vascular endothelial cells supplying blood to cancerous tissues (e.g., tumors, collections of cancerous cells, or other cancerous masses) express an extracellular domain of prostate specific membrane antigen, irrespective of the type of cancer involved. In contrast, vascular endothelial cells supplying blood to normal tissues do not express an extracellular domain of prostate specific membrane antigen.

Another aspect of the present invention relates to a method of detecting normal, benign hyperplastic, and cancerous epithelial cells or portions thereof in a biological sample. This method involves providing a biological agent, such as an antibody or binding portion thereof, probe, or ligand, which binds to an extracellular domain of prostate specific membrane antigen of such cells. The biological agent is bound to a label effective to permit detection of the cells or portions (e.g., prostate specific membrane antigen or fragments thereof liberated from such normal, benign hyperplastic, and cancerous cells) thereof upon binding of the biological agent to the cells or portions thereof. The biological sample is contacted with the biological agent having a label under conditions effective to permit binding of the biological agent to the extracellular domain of the prostate specific membrane antigen of any of the cells or portions thereof in the biological sample. The presence of any cells or portions thereof in the biological sample is detected by detection of the label. In its preferred form, such contacting is carried out in a living mammal and involves administering the biological agent to the mammal under conditions effective to permit binding of the biological agent to the prostate specific membrane antigen of any of the cells or portions thereof in the biological sample. Again, such administration can be carried out orally or parenterally.

The method of the present invention can be used to screen patients for diseases associated with the presence of normal, benign hyperplastic, and cancerous epithelial cells or portions thereof. Alternatively, it can be used to identify the recurrence of such diseases, particularly when the disease is localized in a particular biological material of the patient. For example, recurrence of prostatic disease in the prostatic fossa may be encountered following radical prostatectomy. Using the method of the present invention, this recurrence can be detected by administering a short range radiolabeled antibody to the mammal and then detecting the label rectally, such as with a transrectal detector probe.

Alternatively, the contacting step can be carried out in a sample of serum or urine or other body fluids, such as to detect the presence of PSMA in the body fluid. When the contacting is carried out in a serum or urine sample, it is preferred that the biological agent recognize substantially no antigens circulating in the blood other than PSMA. Since intact prostate cells do not excrete or secrete PSMA into the extracellular environment, detecting PSMA in serum, urine, or other body fluids generally indicates that prostate cells are being lysed. Thus, the biological agents and methods of the present invention can be used to determine the effectiveness of a prostate cancer treatment protocol by monitoring the level of PSMA in serum, urine or other body fluids.

In a particularly preferred embodiment of the method of detecting normal, benign hyperplastic, and cancerous prostate epithelial cells in accordance with the present invention, the biological agent, such as the antibody or binding portion thereof, probe, or ligand, binds to and is internalized with the prostate specific membrane antigen. of such cells. Again, the biological agent is bound to a label effective to permit detection of the cells or portions thereof upon binding of the biological agent to and internalization of the biological agent with the prostate specific membrane antigen.

Another aspect of the present invention relates to a method of detecting cancerous tissue in a biological sample. This method involves providing the above-described biological agent (i.e., a biological agent, such as an antibody or binding portion thereof, probe, or ligand which, when contacted with an extracellular domain of prostate specific-.membrane antigen, recognizes the extracellular domain of prostate specific membrane antigen). The biological agent is bound to a label that is effective to permit detection of vascular endothelial cells proximate to or within the cancerous tissue upon binding of the biological agent to vascular endothelial cells proximate to or within the cancerous tissue. The biological sample is then contacted with the biological agent having a label. Contacting is carried out under conditions effective to permit binding of the biological agent to the vascular endothelial cells proximate to or within the cancerous tissue in the biological sample. The presence of cancerous cells or portions thereof in the biological sample is detected by detection of the label.

Rather than contacting the entire biological sample with the biological agent, it is contemplated that a portion of the biological sample can be used. For example, a tissue biopsy sample can be contacted with the biological agent to determine the presence of cancerous tissue in the tissue biopsy sample as well as in the larger biological sample from which it is taken. Alternatively, the biological agent can be contacted with a serum or urine sample to acertain whether any vascular endothelial cells expressing an extracellular domain of prostate specific membrane antigen are present therein. Since vascular endothelial cells expressing an extracellular domain of prostate specific membrane antigen are found in the vasculature of cancerous tissues but not in the vasculature of normal tissues, detection of the label in a serum or urine sample indicates the presence of cancerous tissue in the larger biological sample from which it is taken (e.g., a patient).

In a particularly preferred embodiment of the method of detecting cancerous tissues in accordance with the present invention, the biological agent employed is one that, when contacted with an extracellular domain of prostate specific membrane antigen, binds to and is internalized with the prostate specific membrane antigen. The methods of the present invention can be used to detect cancerous prostate epithelial cells as well as cancerous tissues containing cancerous cells other than cancerous prostate epithelial cells. Examples of cancerous tissues containing cancerous cells other than cancerous prostate epithelial cells which can be detected with the methods of the present invention include renal, urothelial, colon, rectal, lung, and breast cancerous tissue and cancerous tissue of metastatic adenocarcinoma to the liver.

As indicated above, biological agents suitable for either killing, ablating, or detecting cancerous cells and normal, benign hyperplastic, and cancerous prostate epithelial cells include antibodies, such as monoclonal or polyclonal antibodies. In addition, antibody fragments, half-antibodies, hybrid derivatives, probes, and other molecular constructs may be utilized. These biological agents, such as antibodies, binding portions thereof, probes, or ligands, bind to extracellular domains of prostate specific membrane antigens or portions thereof in normal, benign hyperplastic, and cancerous prostate epithelial cells. As a result, when practicing the methods of the present invention to kill, ablate, or detect normal, benign hyperplastic, and cancerous prostate epithelial cells, the biological agents bind to all such cells, not only to cells which are fixed or cells whose intracellular antigenic domains are otherwise exposed to the extracellular environment. Consequently, binding of the biological agents is concentrated in areas where there are prostate epithelial cells, irrespective of whether these cells are fixed or unfixed, viable or necrotic. Additionally or alternatively, these biological agents, such as antibodies, binding portions thereof, probes, or ligands, bind to and are internalized with prostate specific membrane antigens or portions thereof in normal benign hyperplastic, and cancerous prostate epithelial cells.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in E. Harlow, et. al., editors, *Antibodies: A Laboratory Manual* (1988), which is hereby incorporated by reference.

In addition to utilizing whole antibodies, the processes of the present invention encompass use of binding portions of such antibodies. Such binding portions include Fab fragments, F(ab')$_2$ fragments, and Fv fragments. These antibody fragments can be made by conventional procedures, such as proteolytic fragmentation procedures, as described in J. Goding, *Monoclonal Antibodies: Principles and Practice*, pp. 98–118 (N.Y. Academic Press 1983), which is hereby incorporated by reference.

Alternatively, the processes of the present invention can utilize probes or ligands found either in nature or prepared synthetically by recombinant DNA procedures or other biological or molecular procedures. Suitable probes or ligands are molecules which bind to the extracellular domains of prostate specific membrane antigens identified by the monoclonal antibodies of the present invention. Other suitable probes or ligands are molecules which bind to and are internalized with prostate specific membrane antigens. Such probes or ligands can be, for example, proteins, peptides, lectins, or nucleic acid probes.

It is particularly preferred to use the monoclonal antibodies identified below in Table 1.

TABLE 1

| Monoclonal Antibody Name | ATCC Designation for Hybridoma Cell Line |
| --- | --- |
| E99 | HB-12101 |
| J415 | HB-12109 |
| J533 | HB-12127 |
| J591 | HB-12126 |

These antibodies can be used alone or as a component in a mixture with other antibodies or other biological agents to treat cancers or image cancerous tissues (particularly the vascular endothelial cells therein) or prostate epithelial cells with varying surface antigen characteristics.

Regardless of whether the biological agents are used for treatment or diagnosis, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the biological agent, such as an antibody or binding portion thereof, of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The biological agent of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the biological agent of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The biological agents may be utilized to detect cancerous tissues (particularly the vascular endothelial cells therein) and normal, benign hyperplastic, and cancerous prostate epithelial cells in vivo. This is achieved by labeling the biological agent, administering the labeled biological agent to a mammal, and then imaging the mammal.

Examples of labels useful for diagnostic imaging in accordance with the present invention are radiolabels such as $^{131}I$, $^{111}In$, $^{123}I$, $^{99}mTc$, $^{32}p$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. These isotopes and transrectal detector probes, when used in combination, are especially useful in detecting prostatic fossa recurrences and pelvic nodal disease. The biological agent can be labeled with such reagents using techniques known in the art. For example, see Wensel and Meares, *Radioimmunoimaging and Radioimmunotherapy*, Elsevier, N.Y. (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", *Meth. Enzymol.* 121: 802–816 (1986), which is hereby incorporated by reference.

A radiolabeled biological agent of this invention can be used for in vitro diagnostic tests. The specific activity of a tagged biological agent, such as a tagged antibody, binding portion thereof, probe, or ligand, depends upon the half-life, the isotopic purity of the radioactive label, and how the label is incorporated into the biological agent. Table 2 lists several commonly-used isotopes, their specific activities and half-lives. In immunoassay tests, the higher the specific activity, in general, the better the sensitivity.

TABLE 2

| Isotope | Specific Activity of Pure Isotope (Curies/mole) | Half-Life |
|---|---|---|
| $^{14}C$ | $6.25 \times 10^{1}$ | 5720 years |
| $^{3}H$ | $2.01 \times 10^{4}$ | 12.5 years |
| $^{35}S$ | $1.50 \times 10^{6}$ | 87 days |
| $^{125}I$ | $2.18 \times 10^{6}$ | 60 days |
| $^{32}p$ | $3.16 \times 10^{6}$ | 14.3 days |
| $^{131}I$ | $1.62 \times 10^{7}$ | 8.1 days |

Procedures for labeling biological agents with the radioactive isotopes listed in Table 2 are generally known in the art. Tritium labeling procedures are described in U.S. Pat. No. 4,302,438, which is hereby incorporated by reference. Iodinating, tritium labeling, and $^{35}S$ labeling procedures especially adapted for murine monoclonal antibodies are described by Goding, J. W. (supra, pp 124–126) and the references cited therein, which are hereby incorporated by reference. Other procedures for iodinating biological agents, such as antibodies, binding portions thereof, probes, or ligands, are described by Hunter and Greenwood, *Nature* 144:945 (1962), David et al., *Biochemistry* 13:1014–1021 (1974), and U.S. Pat. Nos. 3,867,517 and 4,376,110, which are hereby incorporated by reference. Radiolabeling elements which are useful in imaging include $^{123}I$, $^{131}I$, $^{111}In$, and $^{99m}Tc$, for example. Procedures for iodinating biological agents are described by Greenwood, F. et al., *Biochem. J.* 89:114–123 (1963) ; Marchalonis, J., *Biochem. J.* 113:299–305 (1969); and Morrison, M. et al., *Immunochemistry*, 289–297 (1971), which are hereby incorporated by reference. Procedures for $^{99m}Tc$-labeling are described by Rhodes, B. et al. in Burchiel, S. et al. (eds.), *Tumor Imaging: The Radioimmunochemical Detection of Cancer*, New York: Masson 111–123 (1982) and the references cited therein, which are hereby incorporated by reference. Procedures suitable for $^{111}In$-labeling biological agents are described by Hnatowich, D. J. et al., *J. Immul. Methods*, 65:147–157 (1983), Hnatowich, D. et al., *J. Applied Radiation*, 35:554–557 (1984), and Buckley, R. G. et al., *F.E.B.S.* 166:202–204 (1984), which are hereby incorporated by reference.

In the case of a radiolabeled biological agent, the biological agent is administered to the patient, is localized to the tumor bearing the antigen with which the biological agent reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp. 65–85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Fluorophore and chromophore labeled biological agents can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science*, 162:526 (1968) and Brand, L. et al., *Annual Review of Biochemistry*, 41:843–868 (1972), which are hereby incorporated by reference. The biological agents can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above are the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Biological agents can be labeled with fluorchromes or chromophores by the procedures described by Goding, J. (supra, pp 208–249). The biological agents can be labeled with an indicating group containing the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body NMR determination is carried out using an apparatus such as one of those described by Pykett, *Scientific American*, 246:78–88 (1982), which is hereby incorporated by reference, to locate and image cancerous tissues (particularly the vascular endothelial cells therein) and prostate epithelial cells.

In cases where it is important to distinguish between regions containing live and dead prostate epithelial cells or to distinguish between live and dead prostate epithelial cells, the antibodies of the present invention (or other biological agents of the present invention), labeled as described above, can be coadministered along with an antibody or other biological agent which recognizes only living or only dead prostate epithelial cells labeled with a label which can be distinguished from the label used to label the subject antibody. By monitoring the concentration of the two labels at various locations or times, spatial and temporal concentration variations of living and dead normal, benign hyperplastic, and cancerous prostate epithelial cells can be ascertained. In particular, this method can be carried out using the labeled antibodies of the present invention, which recognize both living and dead epithelial prostate cells, and labeled 7E11 antibodies, which recognize only dead epithelial prostate cells.

The biological agents can also be utilized to kill or ablate cancerous cells and normal, benign hyperplastic, and cancerous prostate epithelial cells in vivo. This involves using the biological agents by themselves or with a cytotoxic drug to which the biological agents of the present invention (i.e., biological agents recognizing normal, benign hyperplastic, and cancerous prostate epithelial cells) are bound. This involves administering the biological agents bonded to a cytotoxic drug to a mammal requiring such treatment. In the case of normal, benign hyperplastic, and cancerous prostate epithelial cells, since the biological agents recognize prostate epithelial cells, any such cells to which the biological agents bind are destroyed. Although such administration may destroy normal prostate epithelial cells, this is not problematic, because the prostate is not required for life or survival. Although the prostate may indirectly contribute to fertility, this is not likely to be a practical consideration in patients receiving the treatment of the present invention. In the case of cancerous tissues, since the biological agents recognize vascular endothelial cells that are proximate to cancerous cells, binding of the biological agent/cytotoxic drug complex to these vascular endothelial cells destroys them, thereby cutting off the blood flow to the proximate cancerous cells and, thus, killing or ablating these cancerous cells. Alternatively, the biological agents, by virtue of their binding to vascular endothelial cells that are proximate to cancerous cells, are localized proximate to the cancerous cells. Thus, by use of suitable biological agents (including those containing substances effective to kill cells nondiscriminatingly but only over a short range), cells in cancerous tissue (including cancerous cells) can be selectively killed or ablated.

The biological agents of the present invention may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters.

Enzymatically active toxins and fragments. thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the biological agents with the cytotoxic agents have been previously described. Procedures for conjugating chlorambucil with antibodies are described by Flechner, I,. *European Journal of Cancer*, 9:741–745 (1973); Ghose, T. et al., *British Medical Journal*, 3:495–499 (1972); and Szekerke, M., et al., *Neoplasma*, 19:211–215 (1972), which are hereby incorporated by reference. Procedures for conjugating daunomycin and adriamycin to antibodies are described by Hurwitz, E. et al., *Cancer Research*, 35:1175–1181 (1975) and Arnon, R. et al. *Cancer Surveys*, 1:429–449 (1982), which are hereby incorporated by reference. Procedures for preparing antibody-ricin conjugates are described in U.S. Pat. No. 4,414,148 and by Osawa, T., et al. *Cancer Surveys*, 1:373–388 (1982) and the references cited therein, which are hereby incorporated by reference. Coupling procedures as also described in EP 86309516.2, which is hereby incorporated by reference.

In a particularly preferred embodiment of the present invention, especially well-suited for killing or ablating normal, benign hyperplastic, and cancerous prostate epithelial cells, a first biological agent is conjugated with a prodrug which is activated only when in close proximity with a prodrug activator. The prodrug activator is conjugated with a second biological agent according to the present invention, preferably one which binds to a non-competing site on the prostate specific membrane antigen molecule. Whether two biological agents bind to competing or non-competing binding sites can be determined by conventional competitive binding assays. For example, monoclonal antibodies J591, J533, and E99 bind to competing binding sites on the prostate specific membrane antigen molecule. Monoclonal antibody J415, on the other hand, binds to a binding site which is non-competing with the site to which J591, J533, and E99 bind. Thus, for example, the first biological agent can be one of J591, J533, and E99, and the second biological agent can be J415. Alternatively, the first biological agent can be J415, and the second biological agent can be one of J591, J533, and E99. Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," *Cancer Research*, 56:3287–3292 (1996), which is hereby incorporated by reference.

Alternatively, the biological agent can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303–316 (Academic Press 1985), which is hereby incorporated by reference. Other. suitable radioisotopes include α-emitters, such as $^{212}$Bi, $^{213}$Bi, and $^{211}$At, and β-emitters, such as $^{186}$Re and $^{90}$Y. Radiotherapy is expected to be particularly effective, because prostate epithelial cells and vascular endothelial cells within cancers are relatively radiosensitive.

Where the biological agents are used alone to kill or ablate cancerous cells or prostate epithelial cells, such killing or ablation can be effected by initiating endogenous host immune functions, such as complement-mediated or antibody-dependent cellular cytotoxicity.

The biological agent of the present invention can be used and sold together with equipment, as a kit, to detect the particular label.

Biological agents of the present invention can be used in conjunction with other therapeutic treatment modalities. Such other treatments include surgery, radiation, cryosurgery, thermotherapy, hormone treatment, chemotherapy, vaccines, and other immunotherapies.

Also encompassed by the present invention is a method of killing or ablating which involves using the biological agents for prophylaxis. For example, these materials can be used to prevent or delay development or progression of prostate or other cancers.

Use of the therapeutic methods of the present invention to treat prostate and other cancers has a number of benefits. Since the biological agents according to the present invention only target cancerous cells (such as cells of cancerous tissues containing vascular endothelial cells) and prostate epithelial cells, other tissue is spared. As a result, treatment with such biological agents is safer, particularly for elderly patients. Treatment according to the present invention is expected to be particularly effective, because it directs high levels of biological agents, such as antibodies or binding portions thereof, probes, or ligands, to the bone marrow and lymph nodes where prostate cancer metastases and metastases of many other cancers predominate. Moreover, the methods of the present invention are particularly well-suited for treating prostate cancer, because tumor sites for prostate cancer tend to be small in size and, therefore, easily destroyed by cytotoxic agents. Treatment in accordance with the present invention can be effectively monitored with clinical parameters, such as, in the case of prostate cancer, serum prostate specific antigen and/or pathological features of a patient's cancer, including stage, Gleason score, extracapsular, seminal, vesicle or perineural invasion, positive margins, involved lymph nodes, etc. Alternatively, these parameters can be used to indicate when such treatment should be employed.

Because the biological agents of the present invention bind to living prostate cells, therapeutic methods for treating prostate cancer using these biological agents are much more effective than those which target lysed prostate cells. For the same reasons, diagnostic and imaging methods which determine the location of living normal, benign hyperplastic, or cancerous prostate epithelial cells (as well as vascular endothelial cells within cancers) are much improved by employing the biological agents of the present invention. In addition, the ability to differentiate between living and dead prostate cells can be advantageous, especially to monitor the effectiveness of a particular treatment regimen.

Hybridomas E99, J415, J533, and J591 have been deposited pursuant to, and in satisfaction of, the requirements of the Budapest Treaty on the International Recognition of the Deposit of Microorganisms for the Purposes of Patent Procedure with the American Type Culture Collection ("A.T.C.C.") at 12301 Parklawn Drive, Rockville, Md. 20852. Hybridoma E99 was deposited on May 2, 1996, and received A.T.C.C. Designation Number HB-12101. Hybridoma J415 was deposited on May 30, 1996, and received A.T.C.C. Designation Number HB-12109. Hybridomas J533 and J591 were deposited on Jun. 6, 1996, and received A.T.C.C. Designation Numbers HB-12127 and HB-12126, respectively.

The present invention is further illustrated by the following examples.

EXAMPLES

Example 1

Human Tissues

Fresh specimens of benign and malignant tissues were obtained from the Department of Pathology of New York Hospital Cornell University Medical Center ("NYH-CUMC").

Example 2

Tissue Culture

Cultured cell lines of human cancers were obtained from the Laboratory of Urological Oncology of NYH-CUMC. The prostate cancer cell lines PC-3 (Mickey, D. D., et al., "Characterization Of A Human Prostate Adenocarcinoma Cell Line (DU145) As A Monolayer Culture And As A Solid Tumor In Athymic Mice," *Prog. Clin. Biol. Res.*, 37:67–84 (1980), which is hereby incorporated by reference), DU-145 (Mickey, D. D., et al., "Characterization Of A Human Prostate Adenocarcinoma Cell Line (DU145) As A Monolayer Culture And As A Solid Tumor In Athymic Mice," *Prog. Clin. Biol. Res.*, 37:67–84 (1980), which is hereby incorporated by reference), and LNCaP (Horoszewicz, J. S., et al., "LNCaP Model Of Human Prostatic Carcinoma," *Cancer Res.*, 43:1809–1818 (1983), which is hereby incorporated by reference) were obtained from the American Type Culture Collection (Rockville, Md.). Hybridomas were initially cloned in RPMI-1640 medium supplemented with 10% FCS, 0.1 mM nonessential amino acids, 2 mM L-glutamine, 100 units/ml of penicillin, 100 ug/ml of streptomycin and HAT medium (GIBCO, Grand Island, N.Y.). Subclones were cultured in the same medium without aminopterin.

Example 3

PreTaration of Mouse Monoclonal Antibodies

Female BALB/c mice were immunized intraperitoneally with LNCaP ($6 \times 10^6$ cells) three times at 2 week intervals. A final intraperitoneal booster immunization was administered with fresh prostate epithelial cells which had been grown in vitro. Three days later, spleen cells were fused with SP-2 mouse myeloma cells utilizing standard techniques (Ueda, R., et al., "Cell Surface Antigens Of Human Renal Cancer Defined By Mouse Monoclonal Antibodies: Identification Of Tissue-Specific Kidney Glycoproteins," *Proc. Natl. Acad. Sci. USA*, 78:5122–5126 (1981), which is hereby incorporated by reference). Supernatants of the resulting clones were screened by rosette and complement cytotoxicity assays against viable LNCaP. Clones which were positive by these assays were screened by immunochemistry vs normal kidney, colon, and prostate. Clones which were LNCap$^+$/NmlKid$^-$/colon$^-$/prostate$^+$ were selected and subcloned 3 times by limiting dilution. The immunoglobulin class of cultured supernatant from each clone was determined by immunodiffusion using specified rabbit antisera (Calbiochem, San Diego, Calif.). mAbs were purified using the MAPS-II kit (Bio-Rad, Richmond, Calif.)

Example 4

Biotinylation of mAbs

Purified mabs were dialyzed in 0.1 M NaHCO$_3$ for 2 hours. One ml of mAb at 1 mg/ml was mixed with 0.1 ml of biotinamidocaproate N-hydroxysuccinamide ester (Sigma) in dimethylsulfoxide (1 mg/ml) and stirred for 4 hours at room temperature. Unbound biotin was removed by dialysis against phosphate buffered saline ("PBS").

Example 5

Immunohistochemical Staining of Prostate Tissues

Cryostat sections of prostate tissues were placed inside rings of Falcon 3034 plate covers (Becton Dickenson, Lincoln Park, N.J.) previously coated with 0.45% gelatin solution as described in Marusich, M. F., "A Rapid Method For Processing Very Large Numbers Of Tissue Sections For Immunohistochemical Hybridoma Screening," *J. Immunol. Methods*, 111:143–145 (1988), which is hereby incorporated by reference. Plates were stored at −80° C. Cryostat sections were fixed with 2% paraformaldehyde in PBS for l0min at room temperature, and, after washing with PBS, endogenous peroxidase activity was blocked by treatment with 0.3% hydrogen peroxide in PBS for 10 min at room temperature. After sections were incubated with 2% BSA in PBS for 20 min, mAbs were added for 60 min at room temperature. Slides were extensively washed with PBS and incubated with peroxidase-conjugated rabbit anti-mouse Ig (DAKO Corp., Santa Barbara, Calif.) diluted 1:100 in 10% normal human serum in PBS for 60 min at room temperature. After a diaminobenzidine reaction, sections were counterstained with hematoxylin.

Example 6

Serological Analysis

The anti-mouse immunoglobulin mixed hemadsorption assay was performed as described in Ueda, R., et al., "Cell Surface Antigens Of Human Renal Cancer Defined By Mouse Monoclonal Antibodies: Identification Of Tissue-Specific Kidney Glycoproteins," *Proc. Natl. Acad. Sci. USA*, 78:5122–5126 (1981), which is hereby incorporated by reference. To prepare the indicator cells, anti-mouse Ig (DAKO Corp.) was conjugated to type O human RBC using 0.01% chromium chloride. Serological assays were performed on cells previously plated in Terasaki plates (Nunc, Denmark). Antibodies were incubated with target cells at room temperature for 1 hour. Target cells were then washed, and indicator cells added for 1 hour.

Example 7

Immunoprecipitation

LNCaP cells (2×107) were biotinylated with biotin-NHSS (at final concentration of 5 mM) for 30 minutes on ice. After washing, the biotinylated cells were resuspended in 1 ml lysis buffer (20 mM Tris/HCl pH 8.0, 1 mM EDTA, 1 mM PMSF, 1% triton X-100) for 30 min on ice. The suspension was centrifuged at 1500×100 min at 4° C., and the supernatant was centrifuged at 12,000 rpm×15 min at 4° C. The resulting lysate was preabsorbed with rabbit or goat anti-mouse IgG-coated pansorbin for 1 hour at 4° C. The pre-absorbed lysate was incubated with the mAb overnight at 4° C. Rabbit or goat anti-mouse Ig-coated agarose beads were added for 2 hours at 4° C. and then washed. The beads were resuspended in Tris-base/NaCl, added to sample buffer with 2-mercaptoethanol, and boiled for 5 min. After centrifuging, the supernatant was run on an SDS-PAGE 12% gel. The gel was transferred to a nitrocellulose membrane which was blocked and stained with straptavidin-peroxidase. The membrane was developed with diaminobenzidine ("DAB")

Sequential immunoprecipitation was similar except that the lysate was initially pre-cleared with one mAb overnight at 4° C. A second mAb was then used to immunoprecipitate the pre-cleared lysate.

Approximately 2000 clones were screened, of which four clones were selected as described in Example 3, above. After subcloning, supernatants from the 4 hybridomas, E99, J415, J533, and J591, were assayed by immunofluorescence against viable (i.e. unfixed) LNCaP, immunoprecipitation, and sequential immunoprecipitation to confirm reactivity to PSMA.

The immunofluorescence study using the LNCaP target cell (described originally in Horoszewicz, which is hereby incorporated by reference, to make the 7E11 antibody and the prototype cell line for expression for PSMA) shows that E99 antibody binds to and renders viable LNCaP cells immunofluorescent. This is in contrast to the 7E11 antibody, which, as noted originally in Horoszewicz, which is hereby incorporated by reference, gives only poor or no binding to viable LNCaP cells but exhibits strong binding once the cells are fixed (killed).

The reactivities of the four mAbs with normal human tissues were examined immunohistochemically; these results are presented in Table 3.

TABLE 3

Reactivity of mAbs with human normal tissues by indirect immunoperosidase staining

| Tissues | E99 ($\gamma_3$) | J415 ($\gamma_1$) | J533 ($\gamma_1$) | J591 ($\gamma_1$) |
| --- | --- | --- | --- | --- |
| Prostate* | ● | ● | ● | ● |
| Kidney | | | | |
|   Glomerulus | ○ | ○ | ○ | ○ |
|   Prox. Tubule | ■ | ■ | ■ | ■ |
| Ureter | ○ | ○ | ○ | ○ |
| Bladder | ○ | ○ | ○ | ○ |
| Testis | ○ | ○ | ○ | ○ |
| Uterus | ○ | ○ | ○ | ○ |
| Esophagus | ○ | ○ | ○ | ○ |
| Small Intestine | ○ | ○ | ○ | ○ |
| Stomach | ○ | ○ | ○ | ○ |
| Colon | ○ | ○ | ○ | ○ |
| Spleen | ○ | ○ | ○ | ○ |
| Thyroid | ○ | ○ | ○ | ○ |
| Lung | ○ | ○ | ○ | ○ |
| Pancreas | ○ | ○ | ○ | ○ |
| Liver | ○ | ○ | ○ | ○ |
| * BPH | 0–3+ | 0–3+ | 0–4+ | 0–4+ |
| * Prostate Cancer | 0–3+ | 0–3+ | 0–4+ | 0–4+ |
| * LNCaP (scid) | 3+ | 3+ | 4+ | 4+ |
| * LuCaP (scid) | 0–2+ | 0–2+ | 0–3+ | 0–3+ |

● - positive; ■ - weak, heterogeneous; ○ - negative

The above sequential immunoprecipitaion study showed that 7E11, E99, J415, J533, and J591 bind to the same molecule, i.e. PSMA.

Example 8

Western Blot Analysis

To confirm that antibodies E99, J415, J533, and J591 precipitate an identical band to the 7E11 antibody (i.e., PSMA), Western Blot analyses were performed. Seminal plasma (400 µg/lane) or LNCaP lysate were loaded into lanes of 12% SDS-PAGE gels. After electrophoresis, the gels are transferred to nitrocellulose membranes. The membranes were blocked with 5% dry milk/Tris-buffered saline-tween 20 ("TBST") for 60 min at room temperature. After washing, the membranes were incubated with primary mAb for 60 min at room temperature. After repeat washing, the membranes were incubated with sheep anti-mouse-Ig-peroxidase 1/5000 in 5% dry milk/TBST for 60 min at room temperature. After repeat washing, the membranes were developed using a chemiluminescent tag designated "ECL" (Amersham Life Sciences, International, Arlington Heights, Ill.) according to the manufacturer's directions. The results of the Western Blot experiment are presented in Table 4.

TABLE 4

Western blot data

| Sample | 7E11 | E99 | J415 | J533 | J591 |
| --- | --- | --- | --- | --- | --- |
| Prostatic (seminal) fluid | 100 KD band | 100 KD band | 100 KD band | 100 KD band | 100 KD band |
| LNCaP cell lysate | 100 KD & 200 KD bands | 100 KD & 200 KD bands | 100 KD & 200 KD bands | 100 KD & 200 KD bands | 100 KD & 200 KD bands |

Example 9 mAb Reactivity to External Domain of PSMA

To confirm cell surface (external) expression of the detected PSMA, fresh, viable LNCaP cells were tested, without fixation, in vitro, by immunofluorescence. LNCaP cells were washed and incubated with mAb for 1 hour at room temperature and then with a rabbit anti-mouse Ig-fluorescein (DAKO Corp., Santa Barbara, Calif.). Wells were read with a fluorescent microscope. Negative control consisted of an isotype-matched irrelevant mAb, while an anti-class I MHC mAb served as a positive control.

Immunofluorescence and rosette assay results are presented in Table 5.

TABLE 5

Comparison of 7E11 with new mAbs

| LNCaP viable cells | 7E11 | E99 | J415 | J533 | J591 |
| --- | --- | --- | --- | --- | --- |
| Immunofluorescence | neg | 3+ | 3+ | 4+ | 4+ |
| Rosette assay | neg | + | + | + | + |
| LNCaP-fixed | +++ | ++++ | +++ | ++ | +++ |

Example 10

Competition Studies

A competition study was carried out to determine whether J591, J533, E99, and J415 detected the same or different antigenic sites (epitopes) of the prostate specific membrane antigen molecule using the following procedure.

Plates were coated with LNCaP cell line lysate as a source of prostate specific membrane antigen and washed to remove unbound material. "Cold" (unlabeled) monoclonal antibody was incubated on the plate for 1 hour at room temperature to allow binding to its antigenic site. Subsequently, a second monoclonal antibody, labeled either with biotin or $^{125}$I, was added for an additional hour. Plates were washed to remove unbound material. The amount of the second monoclonal antibody bound to the prostate specific membrane antigen-coated plate was determined either by avidin-alkaline phosphatase in an enzyme-linked immunoassay (in the case of biotin-labeled second monoclonal antibody) or by physically counting the well in a gamma counter (in the case of $^{125}$I-labeled second monoclonal antibody). Controls consisted of using the same monoclonal antibody both cold and labeled to define "100% competition" or using monoclonal antibody to a totally different molecule (e.g., monoclonal antibody I-56, which detects inhibin, a prostate related protein different from prostate specific membrane antigen) to define "0% competition".

The results indicated that J591, J533, and E99 each interfere, compete, or block binding of one another but do not block binding of J415 and vice versa. 7E11/CYT356, known to bind PSMA at a different (intracellular) site, did not block any of J591, J533, E99, or J415.

Having pairs of monoclonal antibodies which bind to non-competing sites permits development of antibody sandwich assays for detecting soluble antigens, such as solubilized prostate specific membrane antigen or fragment thereof, in, for example, body fluids. For example, the antigen (e.g., prostate specific membrane antigen or a fragment thereof) could be "captured" from body fluid with J591 and, in another step, detected by labeled J415.

In another setting, e.g. treatment, one could increase antibody binding by using a combination of non-competing monoclonal antibodies. For example, assuming the non-competing sites are each represented once on the prostate specific membrane antigen molecule, adding a combination of J591 plus J415 would bind twice as many monoclonal antibody molecules as either monoclonal antibody alone. Binding two non-competing antigenic binding sites also can result in greater antigen cross-linking and, perhaps, increased internalization. Furthermore, since the two detected sites are physically located on the same prostate specific membrane antigen molecule, the binding of two monoclonal antibody molecules to that single prostate specific membrane antigen molecule puts the two monoclonal antibody molecules in close proximity to each other, a setting which provides optimal drug-prodrug interaction. For example, monoclonal antibody J591 can be conjugated with an inactive pro-drug and J415 can be conjugated with a pro-drug activator. Since prodrug and activator would be bound in close proximity only at the site of prostate specific membrane antigen-expressing cells (e.g., prostate cancer cells), prodrug activation to the active form would occur only at those sites.

Example 11

Microscopy

Confocal microscopy and immuno-electron microscopy demonstrated that E99, J591, J533, and J415 are bound to the cell membrane at clathrin-coated pits and then rapidly internalize into endosomes (cytoplasmic vesicles). FIGS. 1–4 are immuno-electron micrographs which follow the interaction of gold-labeled monoclonal antibody J591 with the cell surface as a function of time. In these figures, the location of the monoclonal antibody is indicated by the black dots.

Figure 2:
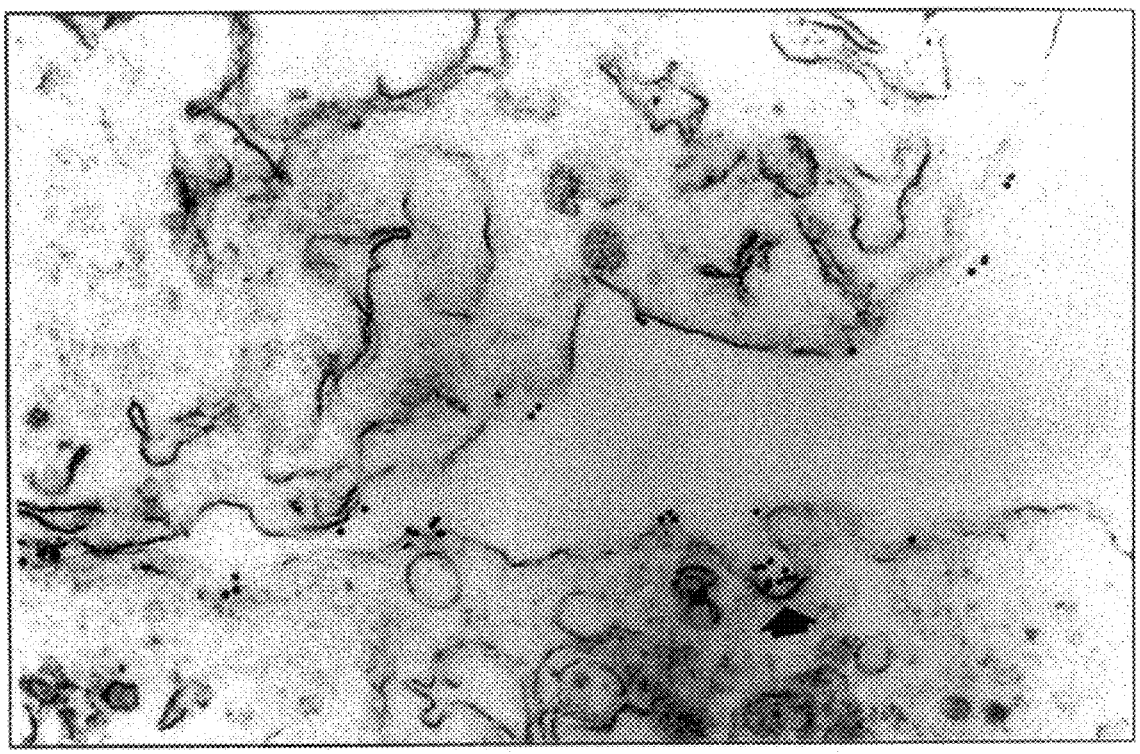
FIG. 2 is an immuno-electron micrograph of LNCaP cells treated with gold-labeled monoclonal antibody J591 after 5 minutes incubation at 37° C.
Figure 3:
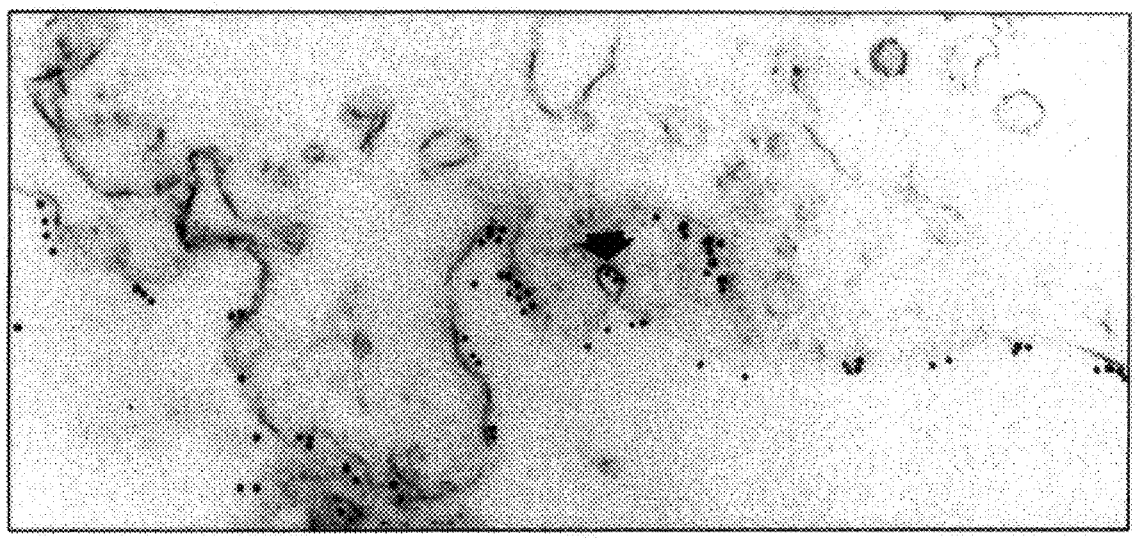
FIG. 3 is an immuno-electron micrograph of LNCaP cells treated with gold-labeled monoclonal antibody J591 after 10 minutes incubation at 37° C.
Figure 4:
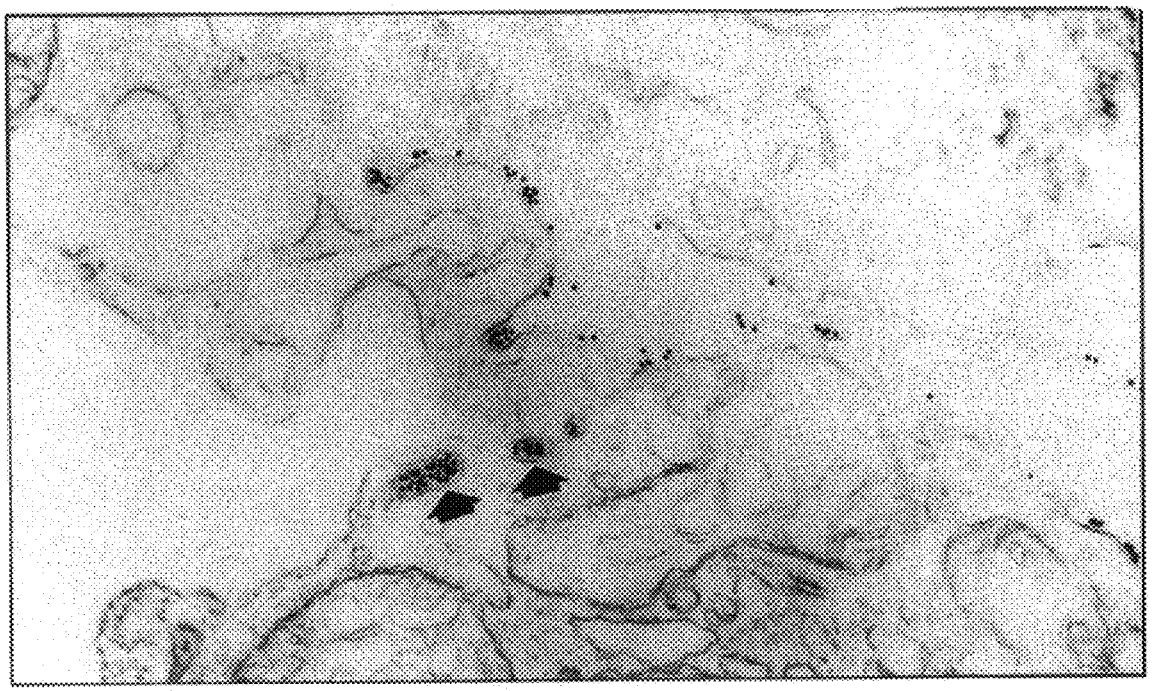
FIG. 4 is an immuno-electron micrograph of LNCaP cells treated with gold-labeled monoclonal antibody J591 after 15 minutes incubation at 37° C.
Figure 5:
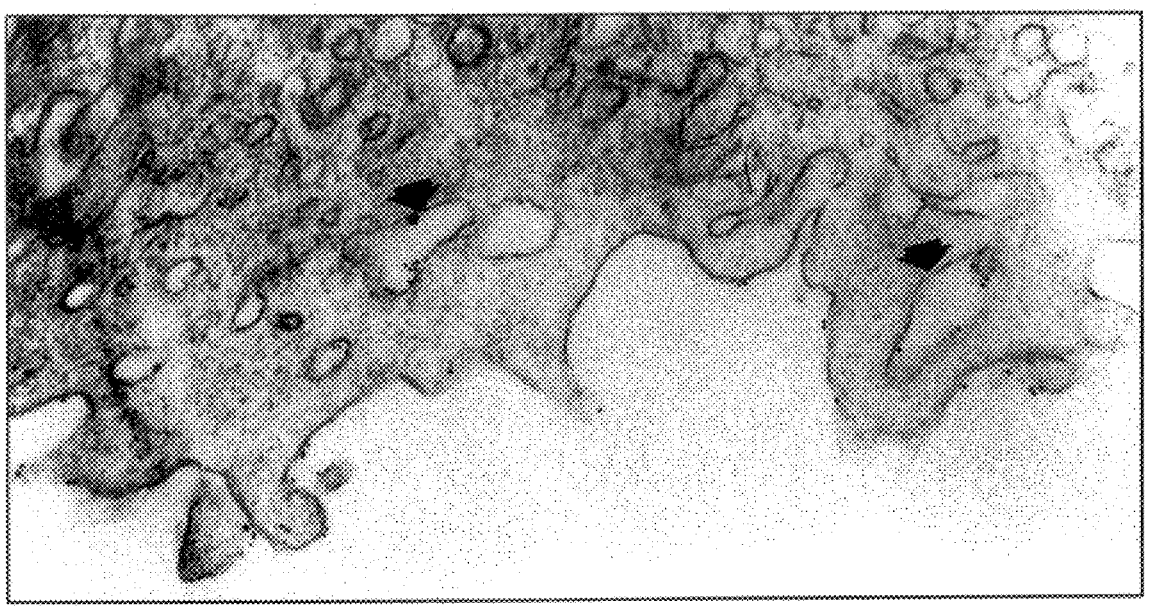
FIG. 5 is an immuno-electron micrograph of LNCaP cells treated with gold-labeled monoclonal antibody J591 after 15 minutes at 37° C. showing J591 within endosomes.

Viable LNCaP cells were incubated with J591 for one hour at 4° C. The cells were washed and then held at 37° C. for 0, 5, 10, or 15 minutes, after which time they were fixed and processed for immuno-electron microscopy. FIG. 1 shows the cell prior to 37° C. incubation. J591 can be seen bound to the cell along the external aspect of the cell membrane. In this Figure, "M" denotes the cell's mitochondria, and "N" denotes its nucleus. FIG. 2 shows the cell after incubation at 37° C. for 5 minutes. The arrow indicates formation of a clathrin-coated pit. In FIG. 3, which shows the cell after a 10 minute 37° C. incubation, pinching off or endocytosis of the clathrin-coated pit can be seen, as indicated by the arrow. FIG. 4 shows that, after incubation at 37° C. for 15 minutes, monoclonal antibody J591 is contained in endocytic vesicles within the cell, as indicated by the arrows. As can be seen in FIG. 5, after incubation at 37° C. for 15 minutes, monoclonal antibody J591 is also contained within endosomes, as indicated by the arrows.

Example 12

Sequencing of the Variable Region of Monoclonal Antibody J591

Total RNA was prepared from $10^7$ murine hybridoma J591 cells. A sample of the conditioned medium from these cells was tested for binding to the specific antigen for J591 on prostate cells. The conditioned medium was positive by both ELISA and Western Blot for binding to the antigen.

VH and VK CDNA were prepared using reverse transcriptase and mouse κ constant region and mouse IgG constant region primers. The first strand cDNAs were amplified by PCR using a variety of mouse signal sequence primers (6 for VH and 7 for VK). The amplified DNAs were gel-purified and cloned into the vector pT7Blue.

The VH and VK clones obtained were screened for correct inserts by PCR, and the DNA sequence of selected clones was determined by the dideoxy chain termination method.

Figure 6:
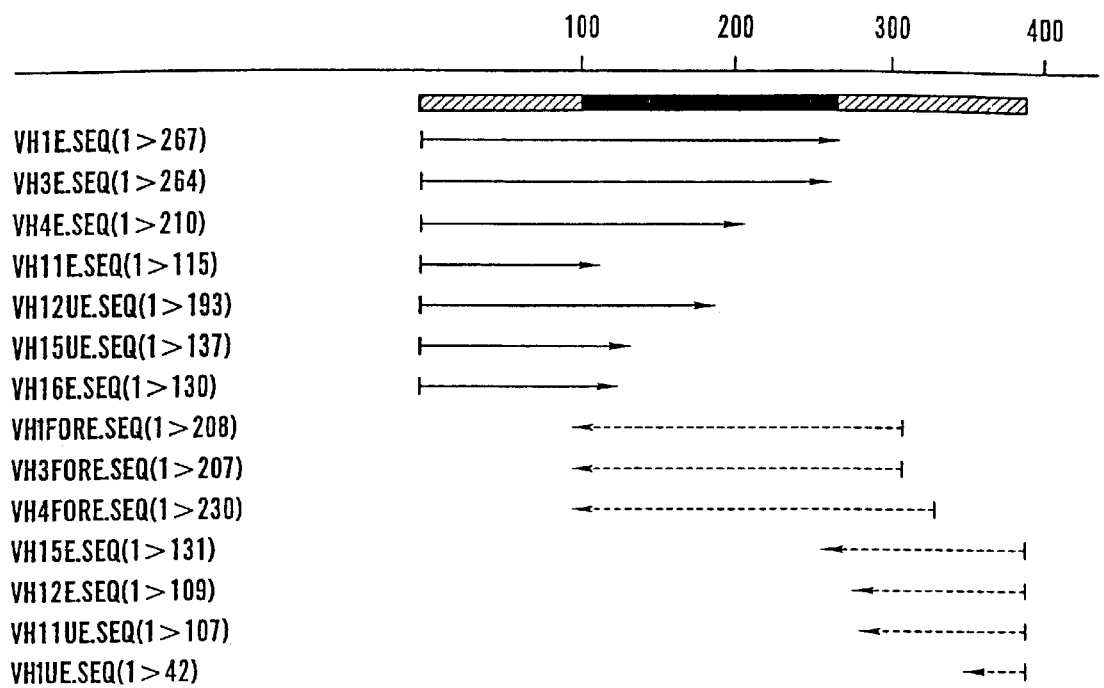
FIG. 6 summarizes the sequencing strategy of the heavy chain of monoclonal antibody J591.
Figure 7:
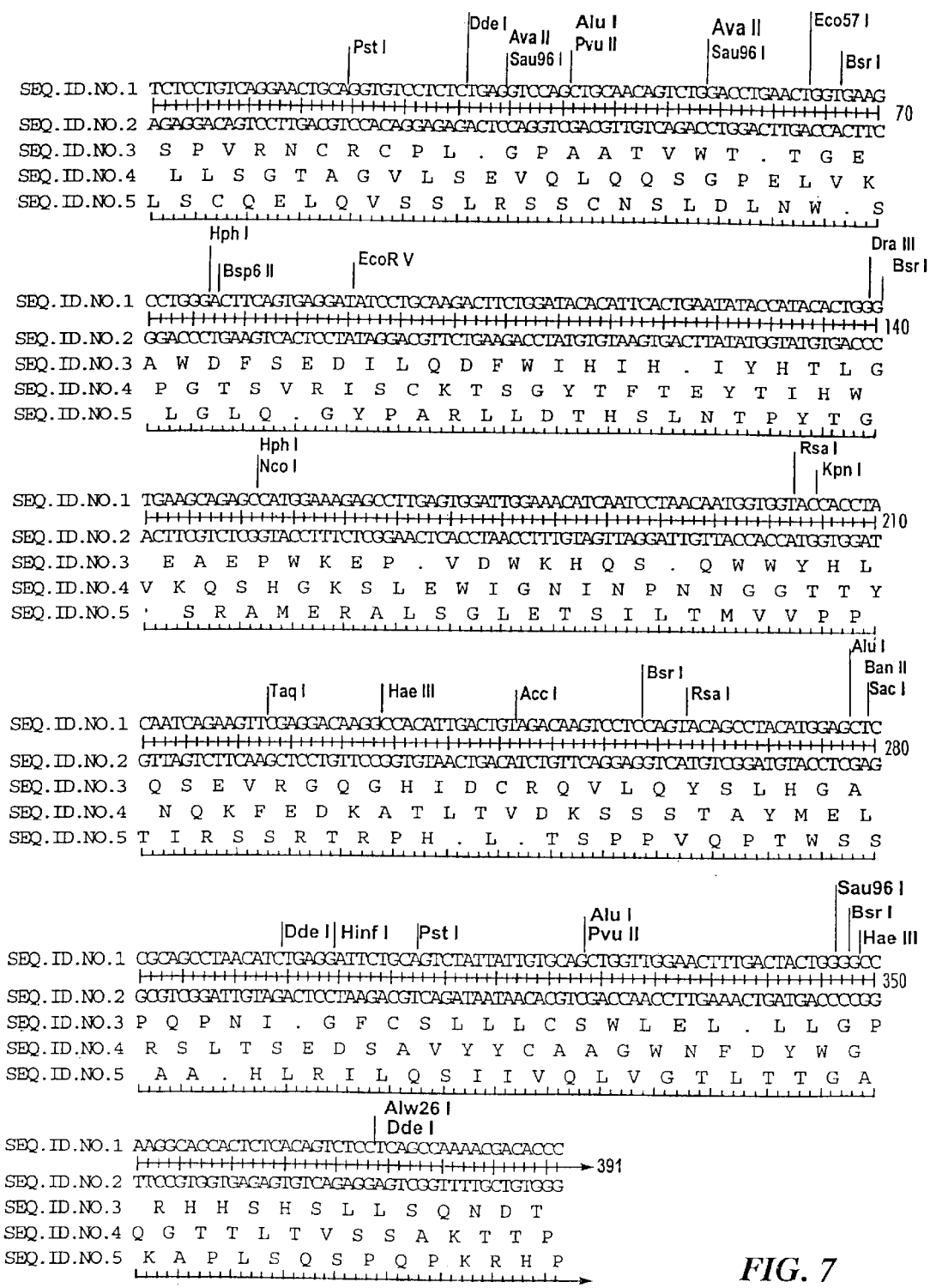
FIG. 7 shows the nucleotide sequence of the heavy chain of monoclonal antibody J591 (designated SEQ.ID. No. 1), the nucleotide sequence of the corresponding reverse, non-coding strand (designated SEQ. ID. No. 2), and the corresponding deduced amino acid sequences (designated SEQ. ID. Nos. 3, 4, and 5)

Excluding the primer region (as the sequence of this depended on the sequence of the primer that was used), all the VH clones obtained gave identical sequence. This sequence was obtained from clones produced with three different 5' primers. One clone had one base pair change within the signal sequence, and one clone contained an aberrant PCR product. Using the sequencing strategy shown in FIG. 6, the nucleotide sequence for the heavy chain was obtained. It is designated SEQ. ID. No. 1 and is presented in FIG. 7, along with the nucleotide sequence of the corresponding reverse, non-coding strand (designated SEQ. ID. No. 2). These sequences include part of the signal sequence and part of the constant region of the antibody. The corresponding deduced amino acid sequences of J591 VH, designated SEQ. ID. No. 3, SEQ. ID. No. 4, and SEQ. ID. No. 5, are also shown in FIG. 7. The coding strand of the J591 heavy chain's variable region (exclusive of signal sequence and constant region components) has the following nucleotide sequence (designated SEQ. ID. No. 6):
GAGGTCCAGCTGCAACAGTCTGGACCT-GAACTGGTGAAGCCTGGGACTTCAGTGAGG ATATCCTGCAAGACTTCTGGATACACAT-TCACTGAATATACCATACAZCTGGGTGAAG CAGAGCCATGGAAAGAGCCTTGAGTG-GATTGGAAACATCAATCCTAACAATGGTGGT ACCACCTACAATCAGAAGTTCGAGGA-CAAGGCCACATTGACTGTAGACAAGTCCTCC AGTACAGCCTACATGGAGCTCCGCAGC-CTAACATCTGAGGATTCTGCAGTCTATTAT TGTG-CAGCTGGTTGGAACTTTGAC-TACTGGGGCCAAGGCACCACTCTCACAGTCTCC TCA The reverse, non-coding strand of the J591 heavy chain's variable region (exclusive of signal sequence and, constant region components) has the following nucleotide sequence (designated SEQ. ID. No. 7):
TGAGGAGACTGTGAGAGTGGTGCCTTG-GCCCCAGTAGTCAAAGTTCCAACCAGCTGC ACAATAATAGACTGCAGAATCCTCAGAT-GTTAGGCTGCGGAGCTCCATGTAGGCTGT ACTG-GAGGACTTGTCTACAGTCAATGTGGCCT-TGTCCTCGAACTTCTGATTGTAGGT GGTACCACCATTGTTAGGATTGAT-GTTTCCAATCCACTCAAGGCTCTTTCCATGGCT CTGCTTCACCCAGTGTATGGTATAT-TCAGTGAATGTGTATCCAGAAGTCTTGCAGGA TATCCTCACTGAAGTCCCAGGCTTCAC-CAGTTCAGGTCCAGACTGTTGCAGCTGGAC CTC The protein sequence corresponding to the J591 heavy chain's variable region (exclusive of signal sequence and constant region components) has the following nucleotide sequence (designated SEQ. ID. No. 8):
EVQLQQSGPELVKPGTSVRISCKTSGYT-FTEYTIHWVKQSHGKSLEWIGNINPNNGG TTYNQK-FEDKATLTVDKSSSTAYMELRSLTSED-SAVYYCAAGWNFDYWGQGTTLTVS The J591 VH is in Mouse Heavy Chains Subgroup IIA (designated SEQ. ID. No. 20)(Kabat et al., *Sequences of Proteins of Immunological Interest*, U.S. Department of Health and Human Services (1991) ("Kabat"), which is hereby incorporated by reference). The sequence of J591 VH is compared to the consensus sequence for this subgroup in FIG. 8.

Figure 9:
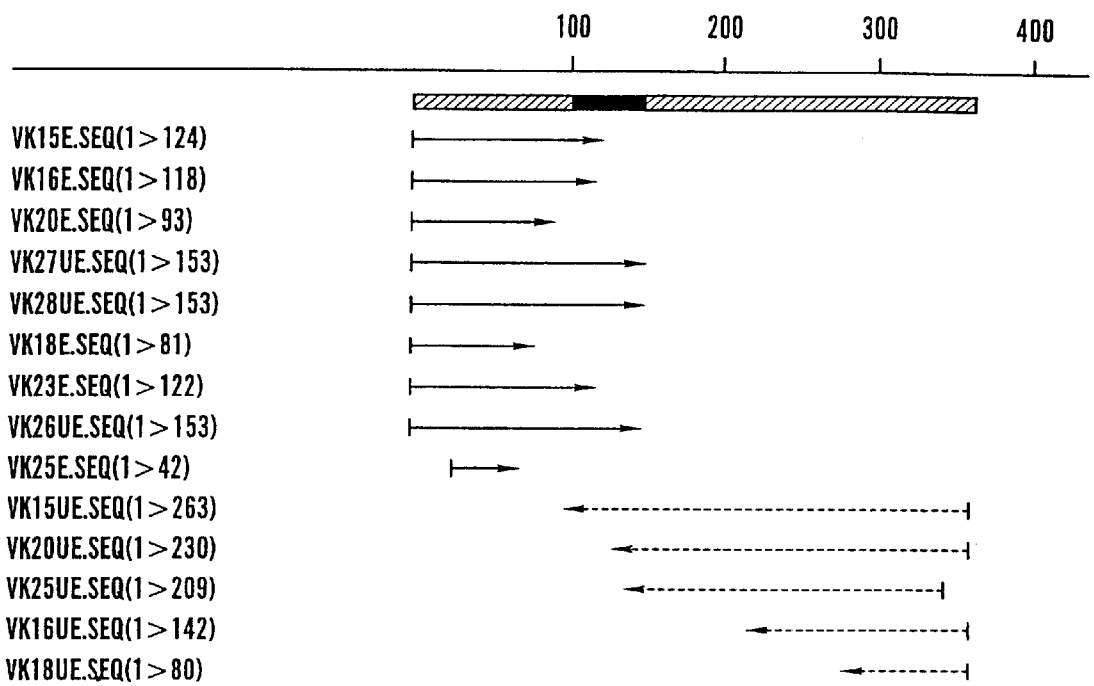
FIG. 9 summarizes the sequencing strategy of the kappa light chain of monoclonal antibody J591.

In contrast to the VH, more than one VK sequence was obtained. Out of the 15 VK clones examined, four gave the sequence of an aberrant mouse-Igκ from the fusion partner (Carol et al., *Molecular Immunolocy*, 25:991–995 (1988), which is hereby incorporated by reference). These clones originated from two specific 5' primers. No further work was done with these clones. Of the remaining clones, ten gave identical nucleotide sequences, and one clone, VK17, gave an alternative VK sequence. The ten identical clones originated from three 5' primers (different from the two that gave the aberrant sequence), one of which also produced VK17. The sequencing strategy that was employed is shown in FIG. 9.

The nucleic acid sequence of J591 VK corresponding to the ten identical clones (designated SEQ. ID. No. 9) is presented in FIG. 10, along with the nucleic acid sequence of the corresponding reverse, non-coding strand (designated SEQ. ID. No. 10) and the deduced amino acid sequences, which are designated SEQ. ID. No. 11, SEQ. ID. No. 12, and SEQ. ID. No. 13. These sequences include part of the signal sequence and part of the constant region of the antibody. The coding strand of the J591 light (kappa) chain's variable region (exclusive of signal sequence and constant region components) corresponding to the ten identical clones has the following nucleotide sequence (designated SEQ. ID. No. 14):
AACATTGTAATGACCCAATCTC-CCAAATCCATGTCCATGTCAGTAGGAGAGAGGGTC ACCTTGACCTGCAAGGCCAGTGAGAAT-GTGGTTACTTATGTTTCCTGGTATCAACAG AAAC-CAGAGCAGTCTCCTAAACTGCT-GATATACGGGGCATCCAACCGGTACACTGGG GTCCCCGATCGCTTCACAGGCAGTG-GATCTGCAACAGATTTCACTCTGACCATCAGC AGT-GTGCAGGCTGAAGACCTTGCAGATTAT-CACTGTGGACAGGGTTACAGCTATCCGC TACACGTTCGGAGGGGGGACCAAGCTG-GAAATAAAA The reverse, non-coding strand of the J591 light (kappa) chain's variable region (exclusive of signal sequence and constant region components) corresponding to the ten identical clones has the following nucleotide sequence (designated SEQ. ID. No. 15):
TTTTATTTCCAGCTTGGTCCCCCCTC-CGAACGTGTACGGATAGCTGTAACCCTGTCC ACAGTGATAATCTGCAAGGTCTTCAGC-CTGCACACTGCTGATGGTCAGAGTGAAATC TGT-TGCAGATCCACTGCCTGTGAAGC-GATCGGGGACCCCAGTGTACCGGTTGGATGC CCCGTATATCAGCAGTTTAGGAGACT-GCTCTGGTTTCTGTTGATACCAGGAAACATA AGTAACCACATTCTCACTGGCCTTGCAG-GTCAAGGTGACCCTCTCTCCTACTGACAT GGA-CATGGATTTGGGAGATTGGGTCATTACAATGTT The protein sequence corresponding to the J591 light (kappa) chain's variable region (exclusive-of signal sequence and constant region components) corresponding to the ten identical clones has the following nucleotide sequence (designated SEQ. ID. No. 16):
NIVMTQSPKSMSMSVGERVTLTCKASEN-VVTYVSWYQQKPEQSPKLLIYGASNRYTG VPDRFTGSGSATDFTLTISSVQAEDLA-DYHCGQGYSYPYTFGGGTKLEIK The coding strand of the J591 light (kappa) chain's variable region (exclusive of signal sequence and constant region components) corresponding to clone VK17 has the following nucleotide sequence (designated SEQ. ID. No. 17):
GACATTGTGATGACCCAGTCTCACAAAT-TCATGTCCACATCAGTAGGAGACAGGGTC AGCAT-CATCTGTAAGGCCAGTCAAGATGTGGG-TACTGCTGTAGACTGGTATCAACAG AAACCAGGACAATCTCCTAAACTACT-GATTTATTGGGCATCCACTCGGCACACTGGA GTC-CCTGATCGCTTCACAGGCAGTG-GATCTGGGACAGACTTCACTCTCACCATTACT AATGTTCAGTCTGAAGACTTGGCAGAT-TATTTCTGTCAGCAATATAACAGCTATCCT CTCACGTTCGGTGCTGGGACCATGCTG-GACCTGAAA The reverse, non-coding strand of the J591 light (kappa) chain's variable region (exclusive of signal sequence and constant region components) corresponding to clone VK17 has the following nucleotide sequence (designated SEQ. ID. No. 18):
TTTCAGGTCCAGCATGGTCCCAGCAC-CGAACGTGAGAGGATAGCTGTTATATTGCTG ACA-GAAATAATCTGCCAAGTCTTCAGACT-GAACATTAGTAATGGTGAGAGTGAAGTC TGTCCCAGATCCACTGCCTGTGAAGC-GATCAGGGACTCCAGTGTGCCGAGTGGATGC CCAATAAATCAGTAGTTTAGGAGAT-TGTCCTGGTTTCTGTTGATACCAGTCTACAGC AGTACCCACATCTTGACTGGCCTTACA-GATGATGCTGACCCTGTCTCCTACTGATGT GGA-CATGAATTTGTGAGACTGGGTCATCACAATGTC The protein sequence corresponding to the J591 light (kappa) chain's variable region (exclusive of signal sequence and constant region components) corresponding to clone VK17 has the following nucleotide sequence (designated SEQ. ID. No. 19):
DIVMTQSHKFMSTSVGDRVSIICKASQD-VGTAVDWYQQKPGQSPKLLIYWASTRHTG VPDRFTGSGSGTDFTLTITNVQSEDLA-DYFCQQYNSYPLTFGAGTMLDLK J591 VK is in the Mouse Kappa Chains Subgroup V (designed SEQ. ID. No. 21)(Kabat, which is. hereby incorporated by reference). The sequence of J591 VK corresponding to the ten identical clones is compared to the consensus sequence for the subgroup in FIG. 11.

Preferred J591's are those having heavy chain variable region DNA coding strand sequences corresponding to SEQ. ID. No. 6 and non-coding strand (reverse) sequences corresponding to SEQ. ID. No. 7. The heavy chain variable region of J591 preferably has an amino acid sequence corresponding to SEQ. ID. No. 8. The light chain variable region of J591 preferably has a DNA coding strand sequence corresponding to SEQ. ID. No. 17, a DNA non-coding strand (reverse) sequence corresponding to SEQ. ID. No. 18, and a amino acid sequence corresponding to SEQ. ID. No. 19.

Example 13

Immunohistochemical Staining of Normal and Cancer Tissues

Cancer tissues from 23 carcinomas were pre-cooled in liquid nitrogen, snap-frozen in OCT compound (Miles, Elkhart, Ind.) on dry ice, and stored at −80° C. Cryostat tissue sections (5 μm) were fixed in cold acetone (4° C.) for 10 minutes. mAbs (5 μg/ml or hybridoma supernatants) were incubated for 1 hour at room temperature. Antibody binding was detected using rabbit anti-mouse Ig-peroxidase (Dako, Carpinteria, Calif.) as a secondary antibody and DAB (Sigma, St. Louis, Mo.) as chromogen. Isotype-matched irrelevant antibody was used as negative control.

mAbs J591, J533, J415, and E99 reacted strongly with vascular endothelia in all 23 carcinomas studied, including 9/9 renal, 5/5 urothelial, 6/6 colon, 1/1 lung, and 1/1 breast carcinomas, and 1/1 metastatic adenocarcinoma to the liver. FIGS. 2A–2F, respectively, show the immunohistochemical reactivity of mAb J591 to neovasculature of renal, urothelial, colon, lung, and breast carcinomas, and metastatic adenocarcinoma to the liver.

Although the invention has been described in detail for the purpose of illustration, it is understood that such detail is solely for that purpose and variations can be made by those skilled in the art without departing from the spirit and scope of the invention which is defined by the following claims.

---

What is claimed:

1. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody.

2. The monoclonal antibody or antigen binding portion thereof of claim 1, wherein the antigen binding portion is selected from the group consisting of a Fab fragment, a F(ab')$_2$ fragment, and a Fv fragment.

3. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein the antibody or antigen-binding portion thereof is bound to a label.

4. A monoclonal antibody or antigen binding portion thereof which binds to an epitope of prostate specific membrane antigen (PSMA) which is also recognized by a monoclonal antibody selected from the group consisting of a E99, a J415, a J533, and a J591 monoclonal antibody, wherein the antibody or antigen-binding portion thereof is bound to a radioisotope.

5. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein said antibody or antigen binding portion thereof is bound to a cytotoxic drug.

6. The monoclonal antibody or antigen binding portion thereof of claim 5, wherein the antigen binding portion is selected from the group consisting of a Fab fragment, a F(ab')$_2$ fragment and a Fv fragment.

7. The monoclonal antibody or antigen binding portion thereof or claim 5, wherein the cytotoxic drug is selected from the group consisting of a therapeutic drug, a toxin, a compound emitting radiation, molecules of plant, fungal, or bacterial origin, biological proteins, and mixtures thereof.

8. The monoclonal antibody or antigen binding portion thereof of claim 5, wherein the cytotoxic drug is a compound which emits radiation.

9. The monoclonal antibody or antigen binding portion thereof of claim 8, wherein the compound which emits radiation is an α, β, or γ-emitter.

10. The monoclonal antibody or antigen binding portion thereof of claim 8, wherein the compound which emits radiation is an α-emitter.

11. The monoclonal antibody or antigen binding portion thereof of claim 10, wherein the α-emitter is selected from the group consisting of $^{212}$Bi, $^{213}$Bi, and $^{211}$At.

12. The monoclonal antibody or antigen binding portion thereof of claim 7, wherein the cytotoxic drug is a molecule of plant, fungal, or bacterial origin.

13. The monoclonal antibody or antigen binding portion thereof of claim 7, wherein the cytotoxic drug is a toxin.

14. The monoclonal antibody or antigen binding portion thereof of claim 7, wherein the cytotoxic drug is a biological protein.

15. A composition comprising:
   a monoclonal antibody or antigen binding portion thereof according to claim 1; and
   a pharmaceutically acceptable carrier, excipient, or stabilizer.

16. A composition comprising:
   a monoclonal antibody or antigen binding portion thereof according to claim 5; and
   a pharmaceutically acceptable carrier, excipient or stabilizer.

17. The monoclonal antibody or antigen binding portion thereof of claim 1, wherein the PSMA is present on prostatic cells.

18. The monoclonal antibody or antigen binding portion thereof of claim 5, wherein the PSMA is present on prostatic cells.

19. The monoclonal antibody or antigen binding portion thereof of claim 1, wherein the PSMA is present on vascular endothelial cells proximate to or within non-prostate cancerous tissue.

20. The monoclonal antibody or antigen binding portion thereof of claim 5, wherein the PSMA is present on vascular endothelial cells proximate to or within non-prostate cancerous tissue.

21. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein said antibody or antigen binding portion thereof is bound to a β-emitter.

22. A monoclonal antibody or antigen binding portion thereof which binds to an epitope of prostate specific membrane antigen (PSMA) which is also recognized by a monoclonal antibody selected from the group consisting of an 1399, a J415, a J533, and a J591 monoclonal antibody, wherein said antibody or antigen binding portion thereof is bound to a γ-emitter.

23. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein said antibody or antigen binding portion thereof is bound to $^{90}$Y.

24. The monoclonal antibody or antigen binding portion thereof of claim 1, wherein the antibody is produced by fusing an antibody secreting immune cell with a myeloma cell or a transformed cell.

25. The monoclonal antibody or antigen binding portion thereof of claim 5, wherein the antibody is produced by fusing an antibody secreting immune cell with a myeloma cell or a transformed cell.

26. The monoclonal antibody or antigen binding portion thereof of claim 21, wherein the antibody is produced by fusing an antibody secreting immune cell with a myeloma cell or a transformed cell.

27. The monoclonal antibody or antigen binding portion thereof of claim 22, wherein the antibody is produced by fusing an antibody secreting immune cell with a myeloma cell or a transformed cell.

28. The monoclonal antibody or antigen binding portion thereof of claim 23, wherein the antibody is produced by fusing an antibody secreting immune cell with a myeloma cell or a transformed cell.

29. The monoclonal antibody or antigen binding portion thereof of claim 1, wherein the antibody or antigen binding portion thereof is internalized with the PSMA.

30. The monoclonal antibody or antigen binding portion thereof of claim 5, wherein the antibody or antigen binding portion thereof is internalized with the PSMA.

31. The monoclonal antibody or antigen binding portion thereof of claim 21, wherein the antibody or antigen binding portion thereof is internalized with the PSMA.

32. The monoclonal antibody or antigen binding portion thereof of claim 22, wherein the antibody or antigen binding portion thereof is internalized with the PSMA.

33. The monoclonal antibody or antigen binding portion thereof of claim 23, wherein the antibody or antigen binding portion thereof is internalized with the PSMA.

34. A composition comprising:
 a monoclonal antibody or antigen binding portion thereof according to claim 21; and
 a pharmaceutically acceptable carrier, excipient, or stabilizer.

35. A composition comprising:
 a monoclonal antibody or antigen binding portion thereof according to claim 22; and
 a pharmaceutically acceptable carrier, excipient, or stabilizer.

36. A composition comprising:
 a monoclonal antibody or antigen binding portion thereof according to claim 23; and
 a pharmaceutically acceptable carrier, excipient, or stabilizer.

37. A kit for detecting cancer comprising:
 a monoclonal antibody or antigen binding portion thereof claim 3 and means to detect the label.

38. The kit of claim 37, wherein the cancer is selected from the group consisting of renal cancer, urothelial cancer, colon cancer, rectal cancer, lung cancer, breast cancer, metastatic adenocarcinoma to the liver, metastatic cancer to the bone marrow, and metastatic cancer to the lymph nodes.

39. A kit according to claim 37, wherein the cancer is prostate cancer.

40. An isolated cell which produces the monoclonal antibody of claim 1.

41. The monoclonal antibody or antigen binding portion thereof of claim 1, wherein said antibody or antigen binding portion thereof binds to an epitope of PSMA which is also recognized by the J591 monoclonal antibody.

42. The monoclonal antibody or antigen binding portion thereof of claim 5, wherein said antibody or antigen binding portion thereof binds to an epitope of PSMA which is also recognized by the J591 monoclonal antibody.

43. The monoclonal antibody or antigen binding portion thereof of claim 21, wherein said antibody or antigen binding portion thereof binds to an epitope of PSMA which is also recognized by the J591 monoclonal antibody.

44. The monoclonal antibody or antigen binding portion thereof of claim 22, wherein said antibody or antigen binding portion thereof binds to an epitope of PSMA which is also recognized by the J591 monoclonal antibody.

45. The monoclonal antibody or antigen binding portion thereof of claim 23, wherein said antibody or antigen binding portion thereof binds to an epitope of PSMA which is also recognized by the J591 monoclonal antibody.

46. A composition comprising:
 a monoclonal antibody or antigen binding portion thereof according to claim 3; and
 a pharmaceutically acceptable carrier, excipient, or stabilizer.

47. The monoclonal antibody or antigen binding portion thereof according to claim 3, wherein the PSMA is present on prostatic cells.

48. The monoclonal antibody or antigen binding portion thereof according to claim 3, wherein the PSMA is present on vascular endothelial cells proximate to or within non-prostate cancerous tissue.

49. The monoclonal antibody or antigen binding portion thereof of claim 3, wherein the antibody is produced by fusing an antibody secreting immune cell with a myeloma cell or a transformed cell.

50. The monoclonal antibody or antigen binding portion thereof of claim 3, wherein the antibody or antigen binding portion thereof is internalized with the PSMA.

51. The monoclonal antibody or antigen binding portion thereof of claim 3, wherein said antibody or antigen binding portion thereof binds to an epitope of PSMA which is also recognized by the J591 monoclonal antibody.

52. The monoclonal antibody or antigen binding portion thereof of claim 1, wherein the antibody or antigen binding portion thereof binds to an epitope of PSMA which is also recognized by the J415 monoclonal antibody.

53. The monoclonal antibody or antigen binding portion thereof of claim 3, wherein the antibody or antigen binding portion thereof binds to an epitope of PSMA which is also recognized by the J415 monoclonal antibody.

54. The monoclonal antibody or antigen binding portion thereof of claim 5, wherein the antibody or antigen binding portion thereof binds to an epitope of PSMA which is also recognized by the J415 monoclonal antibody.

55. The monoclonal antibody or antigen binding portion thereof of claim 21, wherein the antibody or antigen binding portion thereof binds to an epitope of PSMA which is also recognized by the J415 monoclonal antibody.

56. The monoclonal antibody or antigen binding portion thereof of claim 22, wherein the antibody or antigen binding portion thereof binds to an epitope of PSMA which is also recognized by the J415 monoclonal antibody.

57. The monoclonal antibody or antigen binding portion thereof of claim 23, wherein the antibody or antigen binding portion thereof binds to an epitope of PSMA which is also recognized by the J415 monoclonal antibody.

58. The monoclonal antibody or antigen binding portion thereof of claim 21, wherein the β-emitter is selected from the group consisting of $^{186}$Re and $^{90}$Y.

59. The monoclonal antibody or antigen binding portion thereof of claim 4, wherein the radioisotope is selected from the group consisting of $^{131}$I, $^{111}$In, $^{99m}$Tc, $^{32}$P, $^{125}$I, $^{14}$C, and $^{188}$Rh.

60. The monoclonal antibody or antigen binding portion thereof of claim 4, wherein the radioisotope is $^{32}$P, $^{3}$H, $^{14}$C, or $^{188}$Rh.

61. The monoclonal antibody or antigen binding portion thereof of claim 3, wherein the label is selected from the group consisting of a fluorescent label, a biologically-active enzyme label, a nuclear magnetic resonance active label, a luminescent label, and a chromophore label.

62. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein said antibody or antigen binding portion thereof is bound to a cytotoxic drug of bacterial origin.

63. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein said antibody or antigen binding portion thereof is bound to a cytotoxic drug of plant origin.

64. A monoclonal antibody or antigen binding portion thereof which binds to an epitope of prostate specific membrane antigen (PSMA) which is also recognized by a monoclonal antibody selected from the group consisting of an E99, a J415, a J533, and a J591 monoclonal antibody, wherein said antibody or antigen binding portion thereof is bound to a cytotoxic drug of fungal origin.

65. The monoclonal antibody or antigen binding portion thereof of claim 3, wherein the antigen binding portion is selected from the group consisting of a Fab fragment, a F(ab')$_2$ fragment and a Fv fragment.

66. The monoclonal antibody or antigen binding portion thereof of claim 4, wherein the antigen binding portion is selected from the group consisting of a Fab fragment, a F(ab')$_2$ fragment and a Fv fragment.

67. The monoclonal antibody or antigen binding portion thereof of claim 21, wherein the antigen binding portion is selected from the group consisting of a Fab fragment, a F(ab')$_2$ fragment and a Fv fragment.

68. The monoclonal antibody or antigen binding portion thereof of claim 22, wherein the antigen binding portion is selected from the group consisting of a Fab fragment, a F(ab')$_2$ fragment and a Fv fragment.

69. The monoclonal antibody or antigen binding portion thereof of claim 23, wherein the antigen binding portion is selected from the group consisting of a Fab fragment, a F(ab')$_2$ fragment and a Fv fragment.

70. The monoclonal antibody or antigen binding portion thereof of claim 62, wherein the antigen binding portion is selected from the group consisting of a Fab fragment, a F(ab')$_2$ fragment and a Fv fragment.

71. The monoclonal antibody or antigen binding portion thereof of claim 63, wherein the antigen binding portion is selected from the group consisting of a Fab fragment, a F(ab')$_2$ fragment and a Fv fragment.

72. The monoclonal antibody or antigen binding portion thereof of claim 64, wherein the antigen binding portion is selected from the group consisting of a Fab fragment, a F(ab')$_2$ fragment and a Fv fragment.

73. The monoclonal antibody or antigen binding portion thereof according to claim 4, wherein the PSMA is present on prostatic cells.

74. The monoclonal antibody or antigen binding portion thereof according to claim 4, wherein the PSMA is present on vascular endothelial cells proximate to or within non-prostate cancerous tissue.

75. The monoclonal antibody or antigen binding portion thereof according to claim 21, wherein the PSMA is present on prostatic cells.

76. The monoclonal antibody or antigen binding portion thereof according to claim 21, wherein the PSMA is present on vascular endothelial cells proximate to or within non-prostate cancerous tissue.

77. The monoclonal antibody or antigen binding portion thereof according to claim 22, wherein the PSMA is present on prostatic cells.

78. The monoclonal antibody or antigen binding portion thereof according to claim 22, wherein the PSMA is present on vascular endothelial cells proximate to or within non-prostate cancerous tissue.

79. The monoclonal antibody or antigen binding portion thereof according to claim 23, wherein the PSMA is present on prostatic cells.

80. The monoclonal antibody or antigen binding portion thereof according to claim 23, wherein the PSMA is present on vascular endothelial cells proximate to or within non-prostate cancerous tissue.

81. The monoclonal antibody or antigen binding portion thereof according to claim 62, wherein the PSMA is present on prostatic cells.

82. The monoclonal antibody or antigen binding portion thereof according to claim 62, wherein the PSMA is present on vascular endothelial cells proximate to or within non-prostate cancerous tissue.

83. The monoclonal antibody or antigen binding portion thereof according to claim 63, wherein the PSMA is present on prostatic cells.

84. The monoclonal antibody or antigen binding portion thereof according to claim 63, wherein the PSMA is present on vascular endothelial cells proximate to or within non-prostate cancerous tissue.

85. The monoclonal antibody or antigen binding portion thereof according to claim 64, wherein the PSMA is present on prostatic cells.

86. The monoclonal antibody or antigen binding portion thereof according to claim 64, wherein the PSMA is present on vascular endothelial cells proximate to or within non-prostate cancerous tissue.

87. The monoclonal antibody or antigen binding portion thereof of claim 4, wherein the antibody is produced by fusing an antibody secreting immune cell with a myeloma cell or a transformed cell.

88. The monoclonal antibody or antigen binding portion thereof of claim 4, wherein the antibody or antigen binding portion thereof is internalized with the PSMA.

89. The monoclonal antibody or antigen binding portion thereof of claim 4, wherein said antibody or antigen binding portion thereof binds to an epitope of PSMA which is also recognized by the J591 monoclonal antibody.

90. The monoclonal antibody or antigen binding portion thereof of claim 4, wherein the antibody or antigen binding portion thereof binds to an epitope of PSMA which is also recognized by the J415 monoclonal antibody.

91. A composition comprising:
a monoclonal antibody or antigen binding portion thereof according to claim 4; and
a pharmaceutically acceptable carrier, excipient, or stabilizer.

92. A kit for detecting cancer comprising:
a monoclonal antibody or antigen binding portion thereof claim 4 and means to detect the radioisotope.

93. The kit of claim 92, wherein the cancer is selected from the group consisting of renal cancer, urothelial cancer, colon cancer, rectal cancer, lung cancer, breast cancer, metastatic adenocarcinoma to the liver, metastatic cancer to the bone marrow, and metastatic cancer to the lymph nodes.

94. A kit according to claim 92, wherein the cancer is prostate cancer.

95. The monoclonal antibody or antigen binding portion thereof of claim 62, wherein the antibody is produced by fusing an antibody secreting immune cell with a myeloma cell or a transformed cell.

96. The monoclonal antibody or antigen binding portion thereof of claim 62, wherein the antibody or antigen binding portion thereof is internalized with the PSMA.

97. The monoclonal antibody or antigen binding portion thereof of claim 62, wherein said antibody or antigen binding portion thereof binds to an epitope of PSMA which is also recognized by the J591 monoclonal antibody.

98. The monoclonal antibody or antigen binding portion thereof of claim 62, wherein the antibody or antigen binding portion thereof binds to an epitope of PSMA which is also recognized by the J415 monoclonal antibody.

99. The monoclonal antibody or antigen binding portion thereof of claim 63, wherein the antibody is produced by fusing an antibody secreting lymphocyte with a myeloma cell.

100. The monoclonal antibody or antigen binding portion thereof of claim 63, wherein the antibody or antigen binding portion thereof is internalized with the PSMA.

101. The monoclonal antibody or antigen binding portion thereof of claim 63, wherein said antibody or antigen binding portion thereof binds to an epitope of PSMA which is also recognized by the J591 monoclonal antibody.

102. The monoclonal antibody or antigen binding portion thereof of claim 63, wherein the antibody or antigen binding portion thereof binds to an epitope of PSMA which is also recognized by the J415 monoclonal antibody.

103. The monoclonal antibody or antigen binding portion thereof of claim 64, wherein the antibody is produced by fusing an antibody secreting lymphocyte with a myeloma cell.

104. The monoclonal antibody or antigen binding portion thereof of claim 64, wherein the antibody or antigen binding portion thereof is internalized with the PSMA.

105. The monoclonal antibody or antigen binding portion thereof of claim 64, wherein said antibody or antigen binding portion thereof binds to an epitope of PSMA which is also recognized by the J591 monoclonal antibody.

106. The monoclonal antibody or antigen binding portion thereof of claim 64, wherein the antibody or antigen binding portion thereof binds to an epitope of PSMA which is also recognized by the J415 monoclonal antibody.

107. A composition comprising:
a monoclonal antibody or antigen binding portion thereof according to claim 62; and
a pharmaceutically acceptable carrier, excipient, or stabilizer.

108. A composition comprising:
a monoclonal antibody or antigen binding portion thereof according to claim 63; and
a pharmaceutically acceptable carrier, excipient, or stabilizer.

109. A composition comprising:
a monoclonal antibody or antigen binding portion thereof according to claim 64; and
a pharmaceutically acceptable carrier, excipient, or stabilizer.

* * * * *

UNITED STATES PATENT AND TRADEMARK OFFICE
CERTIFICATE OF CORRECTION

| | | |
|---|---|---|
| PATENT NO. | : 6,649,163 B1 | Page 1 of 1 |
| APPLICATION NO. | : 09/357707 | |
| DATED | : November 18, 2003 | |
| INVENTOR(S) | : Neil Bander | |

It is certified that error appears in the above-identified patent and that said Letters Patent is hereby corrected as shown below:

Column 43, line 10, replace "1399" with --E99--;

Column 47, line 18, replace "a monoclonal" with --the monoclonal--;

Column 47, line 19, before "claim", insert --of--.

Signed and Sealed this

Twenty-sixth Day of June, 2007

JON W. DUDAS
*Director of the United States Patent and Trademark Office*

SEQUENCE LISTING

<160> NUMBER OF SEQ ID NOS: 21

<210> SEQ ID NO 1
<211> LENGTH: 391
<212> TYPE: DNA
<213> ORGANISM: Mus sp.

<400> SEQUENCE: 1

```
tctcctgtca ggaactgcag gtgtcctctc tgaggtccag ctgcaacagt ctggacctga      60
actggtgaag cctgggactt cagtgaggat atcctgcaag acttctggat acacattcac     120
tgaatatacc atacactggg tgaagcagag ccatggaaag agccttgagt ggattggaaa     180
catcaatcct aacaatggtg gtaccaccta caatcagaag ttcgaggaca aggccacatt     240
gactgtagac aagtcctcca gtacagccta catggagctc cgcagcctaa catctgagga     300
ttctgcagtc tattattgtg cagctggttg gaactttgac tactggggcc aaggcaccac     360
tctcacagtc tcctcagcca aaacgacacc c                                   391
```

<210> SEQ ID NO 2
<211> LENGTH: 391
<212> TYPE: DNA
<213> ORGANISM: Mus sp.

<400> SEQUENCE: 2

```
gggtgtcgtt ttggctgagg agactgtgag agtggtgcct tggccccagt agtcaaagtt      60
ccaaccagct gcacaataat agactgcaga atcctcagat gttaggctgc ggagctccat     120
gtaggctgta ctggaggact tgtctacagt caatgtggcc ttgtcctcga acttctgatt     180
gtaggtggta ccaccattgt taggattgat gtttccaatc cactcaaggc tctttccatg     240
gctctgcttc acccagtgta tggtatattc agtgaatgtg tatccagaag tcttgcagga     300
tatcctcact gaagtcccag gcttcaccag ttcaggtcca gactgttgca gctggacctc     360
agagaggaca cctgcagttc ctagcaggag a                                   391
```

<210> SEQ ID NO 3
<211> LENGTH: 123
<212> TYPE: PRT
<213> ORGANISM: Mus sp.

<400> SEQUENCE: 3

```
Ser Pro Val Arg Asn Cys Arg Cys Pro Leu Gly Pro Ala Ala Thr Val
1               5                   10                  15

Trp Thr Thr Gly Glu Ala Trp Asp Phe Ser Glu Asp Ile Leu Gln Asp
```

```
                20                  25                  30
Phe Trp Ile His Ile His Ile Tyr His Thr Leu Gly Glu Ala Glu Pro
            35                  40                  45

Trp Lys Glu Pro Val Asp Trp Lys His Gln Ser Gln Trp Trp Tyr His
 50                  55                  60

Leu Gln Ser Glu Val Arg Gly Gln Gly His Ile Asp Cys Arg Gln Val
 65                  70                  75                  80

Leu Gln Tyr Ser Leu His Gly Ala Pro Gln Pro Asn Ile Gly Phe Cys
                85                  90                  95

Ser Leu Leu Cys Ser Trp Leu Glu Leu Leu Gly Pro Arg His
                100                 105                 110

His Ser His Ser Leu Leu Ser Gln Asn Asp Thr
            115                 120
```

<210> SEQ ID NO 4
<211> LENGTH: 130
<212> TYPE: PRT
<213> ORGANISM: Mus sp.

<400> SEQUENCE: 4

```
Leu Leu Ser Gly Thr Ala Gly Val Leu Ser Glu Val Gln Leu Gln Gln
 1               5                  10                  15

Ser Gly Pro Glu Leu Val Lys Pro Gly Thr Ser Val Arg Ile Ser Cys
                20                  25                  30

Lys Thr Ser Gly Tyr Thr Phe Thr Glu Tyr Thr Ile His Trp Val Lys
            35                  40                  45

Gln Ser His Gly Lys Ser Leu Glu Trp Ile Gly Asn Ile Asn Pro Asn
 50                  55                  60

Asn Gly Gly Thr Thr Tyr Asn Gln Lys Phe Glu Asp Lys Ala Thr Leu
 65                  70                  75                  80

Thr Val Asp Lys Ser Ser Thr Ala Tyr Met Glu Leu Arg Ser Leu
                85                  90                  95

Thr Ser Glu Asp Ser Ala Val Tyr Tyr Cys Ala Ala Gly Trp Asn Phe
                100                 105                 110

Asp Tyr Trp Gly Gln Gly Thr Thr Leu Thr Val Ser Ser Ala Lys Thr
            115                 120                 125

Thr Pro
    130
```

<210> SEQ ID NO 5
<211> LENGTH: 125
<212> TYPE: PRT
<213> ORGANISM: Mus sp.

<400> SEQUENCE: 5

```
Leu Ser Cys Gln Glu Leu Gln Val Ser Ser Leu Arg Ser Ser Cys Asn
 1               5                  10                  15

Ser Leu Asp Leu Asn Trp Ser Leu Gly Leu Gln Gly Tyr Pro Ala Arg
                20                  25                  30

Leu Leu Asp Thr His Ser Leu Asn Ile Pro Tyr Thr Gly Ser Arg Ala
            35                  40                  45

Met Glu Arg Ala Leu Ser Gly Leu Glu Thr Ser Ile Leu Thr Met Val
 50                  55                  60

Val Pro Pro Thr Ile Arg Ser Ser Arg Thr Arg Pro His Leu Thr Ser
 65                  70                  75                  80
```

```
Pro Pro Val Gln Pro Thr Trp Ser Ser Ala Ala His Leu Arg Ile Leu
            85                  90                  95

Gln Ser Ile Ile Val Gln Leu Val Gly Thr Leu Thr Thr Gly Ala Lys
            100                 105                 110

Ala Pro Leu Ser Gln Pro Ser Gln Pro Lys Arg His Pro
            115                 120             125
```

<210> SEQ ID NO 6
<211> LENGTH: 345
<212> TYPE: DNA
<213> ORGANISM: Mus sp.

<400> SEQUENCE: 6

```
gaggtccagc tgcaacagtc tggacctgaa ctggtgaagc ctgggacttc agtgaggata      60
tcctgcaaga cttctggata cacattcact gaatatacca tacactgggt gaagcagagc     120
catggaaaga gccttgagtg gattggaaac atcaatccta acaatggtgg taccacctac     180
aatcagaagt tcgaggacaa ggccacattg actgtagaca gtcctccag tacagcctac     240
atggagctcc gcagcctaac atctgaggat tctgcagtct attattgtgc agctggttgg     300
aactttgact actggggcca aggcaccact ctcacagtct cctca                     345
```

<210> SEQ ID NO 7
<211> LENGTH: 345
<212> TYPE: DNA
<213> ORGANISM: Mus sp.

<400> SEQUENCE: 7

```
tgaggagact gtgagagtgg tgccttggcc ccagtagtca agttccaac cagctgcaca       60
ataatagact gcagaatcct cagatgttag gctgcggagc tccatgtagg ctgtactgga    120
ggacttgtct acagtcaatg tggccttgtc ctcgaacttc tgattgtagg tggtaccacc    180
attgttagga ttgatgtttc caatccactc aaggctcttt ccatggctct gcttcaccca    240
gtgtatggta tattcagtga atgtgtatcc agaagtcttg caggatatcc tcactgaagt    300
cccaggcttc accagttcag gtccagactg ttgcagctgg acctc                    345
```

<210> SEQ ID NO 8
<211> LENGTH: 115
<212> TYPE: PRT
<213> ORGANISM: Mus sp.

<400> SEQUENCE: 8

```
Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
            35                  40                  45

Gly Asn Ile Asn Pro Asn Asn Gly Gly Thr Thr Tyr Asn Gln Lys Phe
        50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
```

```
<210> SEQ ID NO 9
<211> LENGTH: 363
<212> TYPE: DNA
<213> ORGANISM: Mus sp.

<400> SEQUENCE: 9
ttatatggag ctgatgggaa cattgtaatg acccaatctc ccaaatccat gtccatgtca      60
gtaggagaga gggtcacctt gacctgcaag gccagtgaga atgtggttac ttatgtttcc     120
tggtatcaac agaaaccaga gcagtctcct aaactgctga tatacggggc atccaaccgg     180
tacactgggg tccccgatcg cttcacaggc agtggatctg caacagattt cactctgacc     240
atcagcagtg tgcaggctga agaccttgca gattatcact gtggacaggg ttacagctat     300
ccgtacacgt tcggaggggg gaccaagctg gaaataaaac gggctgatgc tgcaccaact     360
gta                                                                  363

<210> SEQ ID NO 10
<211> LENGTH: 363
<212> TYPE: DNA
<213> ORGANISM: Mus sp.

<400> SEQUENCE: 10
tacagttggt gcagcatcag cccgttttat ttccagcttg gtccccctc cgaacgtgta       60 cggatagctg taaccctgtc cacagtgata atctgcaagg tcttcagcct gcacactgct     120
gatggtcaga gtgaaatctg ttgcagatcc actgcctgtg aagcgatcgg gaccccagt      180 gtaccggttg gatgccccgt atatcagcag tttaggagac tgctctggtt tctgttgata     240
ccaggaaaca taagtaacca cattctcact ggccttgcag gtcaaggtga ccctctctcc     300
tactgacatg gacatggatt tgggagattg ggtcattaca atgttcccat cagctccata     360
taa                                                                  363

<210> SEQ ID NO 11
<211> LENGTH: 121
<212> TYPE: PRT
<213> ORGANISM: Mus sp.

<400> SEQUENCE: 11

Leu Tyr Gly Ala Asp Gly Asn Ile Val Met Thr Gln Ser Pro Lys Ser
1               5                   10                  15

Met Ser Met Ser Val Gly Glu Arg Val Thr Leu Thr Cys Lys Ala Ser
            20                  25                  30

Glu Asn Val Val Thr Tyr Val Ser Trp Tyr Gln Gln Lys Pro Glu Gln
        35                  40                  45

Ser Pro Lys Leu Leu Ile Tyr Gly Ala Ser Asn Arg Tyr Thr Gly Val
    50                  55                  60

Pro Asp Arg Phe Thr Gly Ser Gly Ser Ala Thr Asp Phe Thr Leu Thr
65                  70                  75                  80

Ile Ser Ser Val Gln Ala Glu Asp Leu Ala Asp Tyr His Cys Gly Gln
                85                  90                  95

Gly Tyr Ser Tyr Pro Tyr Thr Phe Gly Gly Gly Thr Lys Leu Glu Ile
            100                 105                 110

Lys Arg Ala Asp Ala Ala Pro Thr Val
        115                 120
```

<210> SEQ ID NO 12
<211> LENGTH: 114
<212> TYPE: PRT
<213> ORGANISM: Mus sp.

<400> SEQUENCE: 12

Tyr Met Glu Leu Met Gly Thr Leu Pro Asn Leu Pro Asn Pro Cys Pro
1               5                   10                  15

Cys Gln Glu Arg Gly Ser Pro Pro Ala Arg Pro Val Arg Met Trp Leu
            20                  25                  30

Leu Met Phe Pro Gly Ile Asn Arg Asn Gln Ser Ser Leu Leu Asn Cys
        35                  40                  45

Tyr Thr Gly His Pro Thr Gly Thr Leu Gly Ser Pro Ile Ala Ser Gln
    50                  55                  60

Ala Val Asp Leu Gln Gln Ile Ser Leu Pro Ser Ala Val Cys Arg Leu
65                  70                  75                  80

Lys Thr Leu Gln Ile Ile Thr Val Asp Arg Val Thr Ala Ile Arg Thr
                85                  90                  95

Arg Ser Glu Gly Gly Pro Ser Trp Lys Asn Gly Leu Met Leu His Gln
            100                 105                 110

Leu Tyr

<210> SEQ ID NO 13
<211> LENGTH: 116
<212> TYPE: PRT
<213> ORGANISM: Mus sp.

<400> SEQUENCE: 13

Ile Ile Trp Ser Trp Glu His Cys Asn Asp Pro Ile Ser Gln Ile His
1               5                   10                  15

Val His Val Ser Arg Arg Glu Gly His Leu Asp Leu Gln Gly Gln Glu
            20                  25                  30

Cys Gly Tyr Leu Cys Phe Leu Val Ser Thr Glu Thr Arg Ala Val Ser
        35                  40                  45

Thr Ala Asp Ile Arg Gly Ile Gln Pro Val His Trp Gly Pro Arg Ser
    50                  55                  60

Leu His Arg Gln Trp Ile Cys Asn Arg Phe His Ser Asp His Gln Gln
65                  70                  75                  80

Cys Ala Gly Arg Pro Cys Arg Leu Ser Leu Trp Thr Gly Leu Gln Leu
                85                  90                  95

Ser Val His Val Arg Arg Gly Asp Gln Ala Gly Asn Lys Thr Gly Cys
            100                 105                 110

Cys Thr Asn Cys
        115

<210> SEQ ID NO 14
<211> LENGTH: 321
<212> TYPE: DNA
<213> ORGANISM: Mus sp.

<400> SEQUENCE: 14
aacattgtaa tgacccaatc tcccaaatcc atgtccatgt cagtaggaga gagggtcacc      60
ttgacctgca aggccagtga aatgtggtt acttatgttt cctggtatca acagaaacca     120
gagcagtctc ctaaactgct gatatacggg gcatccaacc ggtacactgg ggtccccgat     180
cgcttcacag gcagtggatc tgcaacagat ttcactctga ccatcagcag tgtgcaggct     240

```
gaagaccttg cagattatca ctgtggacag ggttacagct atccgtacac gttcggaggg    300
gggaccaagc tggaaataaa a                                              321
```

<210> SEQ ID NO 15
<211> LENGTH: 321
<212> TYPE: DNA
<213> ORGANISM: Mus sp.

<400> SEQUENCE: 15

```
ttttatttcc agcttggtcc ccctccgaa cgtgtacgga tagctgtaac cctgtccaca     60
gtgataatct gcaaggtctt cagcctgcac actgctgatg gtcagagtga aatctgttgc   120
agatccactg cctgtgaagc gatcggggac cccagtgtac cggttggatg ccccgtatat   180
cagcagttta ggagactgct ctggtttctg ttgataccag gaaacataag taaccacatt   240
ctcactggcc ttgcaggtca aggtgaccct ctctcctact gacatggaca tggatttggg   300
agattgggtc attacaatgt t                                              321
```

<210> SEQ ID NO 16
<211> LENGTH: 107
<212> TYPE: PRT
<213> ORGANISM: Mus sp.

<400> SEQUENCE: 16

```
Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105
```

<210> SEQ ID NO 17
<211> LENGTH: 321
<212> TYPE: DNA
<213> ORGANISM: Mus sp.

<400> SEQUENCE: 17

```
gacattgtga tgacccagtc tcacaaattc atgtccacat cagtaggaga cagggtcagc    60
atcatctgta aggccagtca agatgtgggt actgctgtag actggtatca acagaaacca   120
ggacaatctc ctaaactact gatttattgg gcatccactc ggcacactgg agtccctgat   180
cgcttcacag gcagtggatc tggacagac ttcactctca ccattactaa tgttcagtct    240
gaagacttgg cagattattt ctgtcagcaa tataacagct atcctctcac gttcggtgct   300
gggaccatgc tggacctgaa a                                              321
```

<210> SEQ ID NO 18
<211> LENGTH: 321
<212> TYPE: DNA
<213> ORGANISM: Mus sp.

<400> SEQUENCE: 18

```
tttcaggtcc agcatggtcc cagcaccgaa cgtgagagga tagctgttat attgctgaca      60
gaaataatct gccaagtctt cagactgaac attagtaatg gtgagagtga agtctgtccc     120
agatccactg cctgtgaagc gatcagggac tccagtgtgc cgagtggatg cccaataaat     180
cagtagttta ggagattgtc ctggtttctg ttgataccag tctacagcag tacccacatc     240
ttgactggcc ttacagatga tgctgaccct gtctcctact gatgtggaca tgaatttgtg     300
agactgggtc atcacaatgt c                                               321
```

<210> SEQ ID NO 19
<211> LENGTH: 107
<212> TYPE: PRT
<213> ORGANISM: Mus sp.

<400> SEQUENCE: 19

```
Asp Ile Val Met Thr Gln Ser His Lys Phe Met Ser Thr Ser Val Gly
1               5                   10                  15
Asp Arg Val Ser Ile Ile Cys Lys Ala Ser Gln Asp Val Gly Thr Ala
            20                  25                  30
Val Asp Trp Tyr Gln Gln Lys Pro Gly Gln Ser Pro Lys Leu Leu Ile
        35                  40                  45
Tyr Trp Ala Ser Thr Arg His Thr Gly Val Pro Asp Arg Phe Thr Gly
    50                  55                  60
Ser Gly Ser Gly Thr Asp Phe Thr Leu Thr Ile Thr Asn Val Gln Ser
65                  70                  75                  80
Glu Asp Leu Ala Asp Tyr Phe Cys Gln Gln Tyr Asn Ser Tyr Pro Leu
                85                  90                  95
Thr Phe Gly Ala Gly Thr Met Leu Asp Leu Lys
            100                 105
```

<210> SEQ ID NO 20
<211> LENGTH: 125
<212> TYPE: PRT
<213> ORGANISM: Mus sp.

<400> SEQUENCE: 20

```
Glu Val Gln Leu Gln Gln Ser Gly Pro Glu Leu Val Lys Pro Gly Ala
1               5                   10                  15
Ser Val Lys Ile Ser Cys Lys Ala Ser Gly Tyr Thr Phe Thr Asp Tyr
            20                  25                  30
Tyr Met Asn Asn Trp Val Lys Gln Ser Pro Gly Lys Ser Leu Glu Trp
        35                  40                  45
Ile Gly Asp Ile Asn Pro Gly Asn Gly Gly Thr Ser Tyr Asn Gln Lys
    50                  55                  60
Phe Lys Gly Lys Ala Thr Leu Thr Val Asp Lys Ser Ser Ser Thr Ala
65                  70                  75                  80
Tyr Met Gln Leu Ser Ser Leu Thr Ser Glu Asp Ser Ala Val Tyr Tyr
                85                  90                  95
Cys Ala Arg Gly Tyr Tyr Ser Ser Ser Tyr Met Ala Tyr Tyr Ala Phe
            100                 105                 110
Asp Tyr Trp Gly Gln Gly Thr Thr Val Thr Val Ser Ser
        115                 120                 125
```

<210> SEQ ID NO 21
<211> LENGTH: 109

-continued

```
<212> TYPE: PRT
<213> ORGANISM: Mus sp.

<400> SEQUENCE: 21

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Asp Ile Ser Asn
            20                  25                  30

Tyr Leu Asn Trp Tyr Gln Gln Lys Pro Gly Gly Ser Pro Lys Leu Leu
        35                  40                  45

Ile Tyr Tyr Ala Ser Arg Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Pro Arg Thr Phe Gly Gly Gly Thr Lys Leu Glu Ile Lys
            100                 105
```